US007892740B2

(12) United States Patent
Weichselbaum et al.

(10) Patent No.: US 7,892,740 B2
(45) Date of Patent: Feb. 22, 2011

(54) PROGNOSIS AND THERAPY PREDICTIVE MARKERS AND METHODS OF USE

(75) Inventors: Ralph Weichselbaum, Chicago, IL (US); Bernard Roizman, Chicago, IL (US); Andy Minn, Chicago, IL (US); Nikolai Khodarev, Villa Park, IL (US); Edwardine Labay, Des Plaines, IL (US)

(73) Assignee: The University of Chicago, Chicago, IL (US)

( * ) Notice: Subject to any disclaimer, the term of this patent is extended or adjusted under 35 U.S.C. 154(b) by 79 days.

(21) Appl. No.: 12/087,964

(22) PCT Filed: Jan. 19, 2007

(86) PCT No.: PCT/US2007/060783

§ 371 (c)(1),
(2), (4) Date: Sep. 8, 2008

(87) PCT Pub. No.: WO2007/084992

PCT Pub. Date: Jul. 26, 2007

(65) Prior Publication Data

US 2009/0011439 A1    Jan. 8, 2009

Related U.S. Application Data

(60) Provisional application No. 60/760,313, filed on Jan. 19, 2006.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| 2005/0186577 A1 | 8/2005 | Wang |
| 2008/0187909 A1* | 8/2008 | Dai et al. ........................ 435/6 |

FOREIGN PATENT DOCUMENTS

| WO | WO 2005/054510 | 6/2005 |
| WO | WO 2005/083429 | 9/2005 |
| WO | WO 2005/086891 | 9/2005 |
| WO | WO 2005/100606 | 10/2005 |

OTHER PUBLICATIONS

Muller-Tidow et al (Cancer Lett, 2003, 190(1): Abstract).*
Tockman et al (Cancer Res., 1992, 52:2711s-2718s).*
Alberts et al. (Molecular Biology of the Cell, 3rd edition, 1994, p. 465).*
Greenbaum et al. (Genome Biology, 2003, vol. 4, Issue 9, pp. 117.1-117.8).*
Widschwendter et al (Clinical Cancer Research, 2002, 8:3065-3074).*

Aggarwal, B.B., "Signalling pathways of the TNF superfamily: a double-edged sword," Nat. Rev. Immunol. (2003) 3:745-756.
Akyerli, C.B. et al., "Expression of IFITM1 in chronic myeloid leukemia patients," Leuk. Res. (2005) 29:283-286.
Andersen, J.B. et al., "Interaction between the 2'-5' oligoadenylate synthetase-like protein p59 OASL and the transcriptional repressor methyl CpG-binding protein 1," Eur. J. Biochem. (2004) 271:628-636.
Arany, I. et al., "Differentiation-dependent expression of signal transducers and activators of trasncription (STATs) might modify responses to growth factors in the cancers of the head and neck," Cancer Lett. (2003) 199:83-89.
Banath, J.P. et al., "Expression of phosphorylated histone H2AX as a surrogate of cell killing by drugs that create DNA double-strand breaks," Cancer Res. (2003) 63:4347-4350.
Beyaert, R. et al., "Signaling to gene activiation and cell death by tumor necrosis factor receptors and Fas," Int. Rev. Cytol. (2002) 214:225-272.
Chang, H. et al., "Robustness, scalability, and integration of a wound-response gene expression signature in predicting breast cancer survival," Proc. Natl. Acad. Sci. USA (2005) 102:3738-3743.
Cortes, C. et al., "Support vector networks," Machine Learning (1995) 20:273-297.
Fan, C. et al., "Concordance among gene-expression-based predictors for breast cancer," New Engl. J. Med. (2006) 355:560-569.
Friedberg, J.W. et al., "Oral fludarabine has significant activity in patients with previously untreated chronic lymphocytic leukemia, and leads to increased STAT1 levels in vivo," Leuk. Res. (2004) 28:139-147.
Glinsky, G.V. et al., "Classification of human breast cancer using gene expression profiling as a component of the survival predictor algorithm," Clin. Cancer Res. (2004) 10:2272-2283.
Gupta, A.K. et al., "Local recurrence in head and neck cancer: relationship to radiation resistance and signal transduction," Clin. Cancer Res. (2002) 8:885-892.
Hamilton, S. et al., "Computed tomographic volumetric analysis as a predictor of local control in laryngeal cancers treated with conventional radiotherapy," J. Otalaryngol. (2004) 33:289-294.
Hasina, R. et al., "Plasminogen activator inhibitor-2: a molecular biomarker for head and neck cancer progression," Cancer Res. (2003) 63:555-559.
Kattan, M.W., "Evaluating a new markers predictive contribution," Clin. Cancer Res. (2004) 10:822-824.
Khodarev, N.N. et al., "STAT1 is overexpressed in tumors selected for radioresistance and confers protection from radiation in transduced sensitive cells," Proc. Natl. Acad. Sci. USA (2004) 101:1714-1719.

(Continued)

Primary Examiner—Sean E Aeder
(74) *Attorney, Agent, or Firm*—Andrus, Sceales, Starke & Sawall, LLP

(57) ABSTRACT

Disclosed is a set of genes differentially expressed in chemotherapy and radiation resistant tumors useful in predicting response to therapy and assessing risk of local-regional failure, survival and metastasis in cancer patients. Also disclosed are methods for characterizing tumors according to gene expression and kits for use in the methods of the invention.

23 Claims, 12 Drawing Sheets

OTHER PUBLICATIONS

Khodarev, N.N. et al., "Signal transducer and activator of transcription 1 regulates both cytotoxic and prosurvival functions in tumor cells," Cancer Res. (2007) 67(19):9214-9220.

Kim, H.J. et al., "Identification of retinoid-modulated proteins in squamous carcinoma cells using high-throughput immunoblotting," Cancer Res. (2004) 64:2439-2448.

Kimchi, E.T. et al., "Progression of Barrett's metaplasia to adenocarcinoma is associated with the suppression of the transcriptional programs of epidermal differentiation," Cancer Res. (2005) 65:3146-3154.

Klampfer, L. et al., "Oncogenic Ki-Ras inhibits the expression of interferon-responsive genes through inhibition of STAT1 and STAT2 expression," J. Biol. Chem. (2003) 278:46278-46287.

Levy, D.E. et al., "Stats: transcriptional contorl and biological impact," Nat. Rev. Mol. Cell. Biol. (2002) 3:651-662.

Levy, D.E. et al., "Divergent roles of STAT1 and STAT5 in malignancy as revealed by gene disruptions in mice," Oncogene (2000) 19:2505-2510.

Lin, H.K. et al., "Deregulated TGF-β signaling in leukemogenesis," Oncogene (2005) 24:5693-5700.

Minn, A.J. et al., "Genes that mediate breast cancer metastasis to lung," Nature (2005) 436:518-523.

Paik, S. et al., "A multigene assay to predict recurrence of tamoxifen-treated, node-negative breast cancer," New Engl. J. Med. (2004) 351:2817-2826.

Perou, C.M. et al., "Molecular portraits of human breast tumors," Nature (2000) 406:747-752.

Perou, C.M. et al., "Distinctive gene expression patterns in human mammary epithelial cells and breast cancers," Proc. Natl. Acad. Sci. USA (1999) 96:9212-9217.

Ramana, C.V. et al., "Stat1-dependent and -independent pathways in IFN-γ-dependent signaling," Trends Immunol. (2002) 23:96-101.

Rickardson, L. et al., "Identification of molecular mechanisms for cellular drug resistance by combining drug activity and gene expression profiles," Br. J. Cancer (2005) 93:483-492.

Roberts, D. et al., "Identification of genes associated with plantinum drug sensitivity and resistance in human ovarian cancer cells," Br. J. Cancer (2005) 92:1149-1158.

Russell, N.S. et al., "Radiotherapy: the last 25 years," Cancer Treat. Rev. (1999) 25:365-376.

Saeed, A.I. et al., "TM4: a free, open-source system for microarray data management and analysis," Biotechniques (2003) 34:374-378.

Salloum, R.M. et al., "NM-3, an isocoumarin, increases the antitumor effects of radiotherapy without toxicity," Cancer Res. (2000) 60:6958-6963.

Samuel, C.E., "Antiviral actions of interferons," Clin. Microbiol. Rev. (2001) 14:778-809.

Simon, R., "Roadmap for developing and validating therapeutically relevant genomic classifiers," J. Clin. Oncol. (2005) 23:7332-7341.

Sorlie, T. et al., "Repeated observation of breast tumor subtypes in independent gene expression data sets," Proc. Natl. Acad. Sci. USA (2003) 100:8418-8423.

Spiekermann, K. et al., "Constitutive activation of STAT transcription factors in acute myelogenous leukemia," Eur. J. Haematol. (2001) 67:63-71.

Tan, A.C. et al., "Simple decision rules for classifying human cancers from gene expression profiles," Bioinformatics (2005) 21:3896-3904.

Tibshirani, R. et al., "Diagnosis of multiple cancer types by shrunken centroids of gene expression," Proc. Natl. Acad. Sci USA (2002) 99:6567-6572.

Townsend, P.A. et al., "STAT-1 interacts with p53 to enhance DNA damage-induced apoptosis," Biol. Chem. (2004) 279:5811-5820.

Van De Vijver, M.J. et al., "A gene-expression signature as a predictor of survival in breast cancer," N. Engl. J. Med. (2002) 347:1999-2009.

Van't Veer, L.J. et al., "Gene expression profiling predicts clinical outcome of breast cancer," Nature (2002) 415:530-536.

Weichselbaum, R.R. et al., "Radioresistant tumor cell lines derived from head and neck radiation failures," Head Neck (1989) 11:343-348.

Weichselbaum, R.R. et al., "An interferon-related gene signature for DNA damage resistance is a predictive marker for chemotherapy and radiation for breast cancer," Proc. Natl. Acad. Sci. USA (2008) 105(47):18490-18495.

Widschwendter, A. et al., "Prognostic significance of signal transducer and activator of transcription 1 activation in breast cancer," Clin. Cancer Res. (2002) 8:3065-3074.

Xu, L. et al., "Robust prostate cancer marker genes emerge from direct integration of inter-study microarray data," Bioinformatics (2005) 21:3905-3911.

Yao, R. et al., "Differentially expressed genes associated with mouse lung tumor progression," Oncogene (2002) 21:5814-5821.

International Search Report and Written Opinion of Application No. PCT/US2007/060783 dated Nov. 14, 2007.

* cited by examiner

US 7,892,740 B2

PROGNOSIS AND THERAPY PREDICTIVE MARKERS AND METHODS OF USE

STATEMENT REGARDING FEDERALLY SPONSORED RESEARCH

This invention was made with government support under CA113662 and CA071933 awarded by the National Institute of Health. The government has certain rights in the invention.

CROSS-REFERENCE TO RELATED APPLICATIONS

This application is a national stage filing under 35 U.S.C. 371 of International Application No. PCT/US2007/060783 filed Jan. 19, 2007, which claims priority to U.S. Provisional Patent Application No. 60/760,313 filed Jan. 19, 2006, which are incorporated herein by reference in their entireties.

INTRODUCTION

Clinical management of cancer can be aided by prognosis markers and by therapy predictive markers for chemotherapy and radiation therapy. Prognosis markers assess risk of disease progression independent of therapy. Therapy predictive markers indicate sensitivity or resistance of a cancer to a specific treatment. For most cancers and cancer treatments, there exist subsets of patients that will respond to a particular treatment and subsets of patients that will fail to respond to the treatment.

The use of predictive markers to identify subsets of patients likely to respond to treatment would facilitate selection of appropriate treatment and avoid unnecessary delays associated with ineffective treatment. Additionally, because most cancer treatments are associated with adverse side effects inherent to the treatment, predictive markers eliminate unnecessary risk of adverse side effects by reducing administration of cancer treatments to individuals for whom treatment is likely to fail.

Currently, the only recommended predictive markers in oncology are ER (estrogen receptor) and PR (progesterone receptor) status for selecting endocrine sensitive breast cancers and HER-2 for identifying breast cancer patients with metastatic disease who may benefit from trastuzumab. For malignancies other than breast cancer, validated predictive markers do not exist.

There is a need in the art for additional therapeutic predictive markers for assessing sensitivity or resistance of a cancer to treatment.

SUMMARY OF THE INVENTION

In one aspect, the invention provides a method of characterizing a tumor. The method includes detecting expression of at least one marker of IRDS by a tumor.

In another aspect, the invention provides a kit for performing the method of characterizing a tumor. The kit comprises a probe for detecting expression of the IRDS marker.

In yet another aspect, the invention provides a method for identifying a gene signature marker. The expression of the gene signature marker is correlated with clinical outcome. The method includes developing a radiation or chemotherapeutic resistance cell line from a sensitive cell line, identifying genes differentially expressed between the resistant and sensitive cell line wherein the differentially expressed genes form a resistance gene signature, determining the resistance gene signature status of tumors from a population of humans, and correlating the resistance gene status with clinical outcome.

DETAILED DESCRIPTION OF SEVERAL EMBODIMENTS

Figure 1:
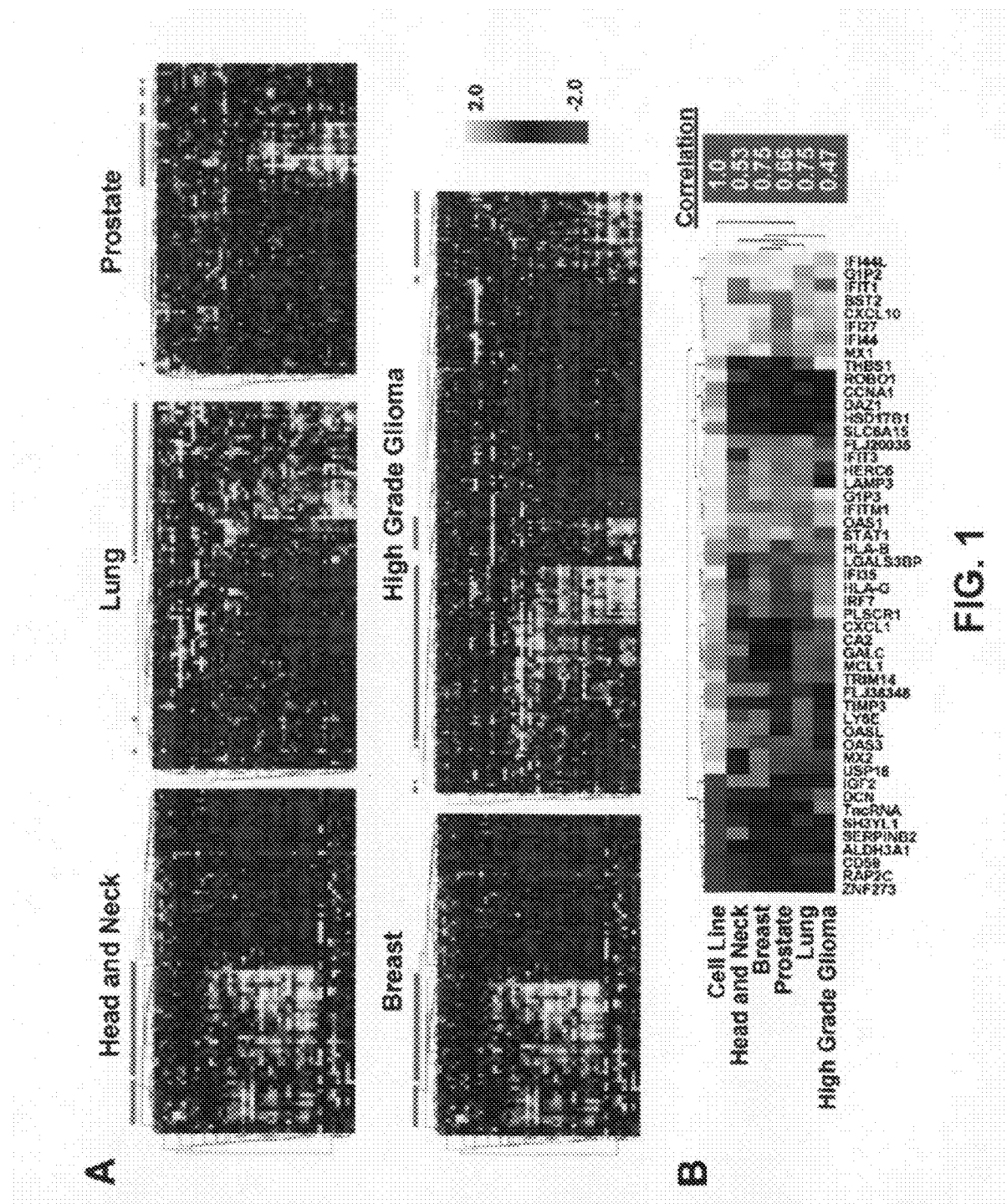
FIG. 1A shows the expression pattern of the IRDS gene signature in a variety of human cancers.
FIG. 1B shows the hierarchical clustering of examples from different human tumors with the 49 genes of the IRDS gene signature with the calculated Pearson correlation coefficient.

A gene signature associated with an interferon signaling pathway, which mediates resistance to DNA damage, was discovered in an experimentally-derived radioresistant tumor cell line obtained by repeated passaging of a radiosensitive human cancer cell line in a mouse model system (Khodarev, N. et al., PNAS, 101:1714-1719 (1994), incorporated herein by reference). Members of the gene signature, designated IRDS (Interferon-Related DNA damage resistance gene Signature), are listed in Table 1. The IFN-stimulated genes of the IRDS were found to be differentially expressed in the radioresistant tumor cell line, relative to the radiosensitive cell line, with most differentially expressed genes exhibiting increased

TABLE 1

IRDS Gene Signature.

| ID | NAME | Symbol | R nu61/ scc61 |
|---|---|---|---|
| 204439_at | interferon-induced protein 44-like | IFI44L | 33.479 |
| 201641_at | bone marrow stromal cell antigen 2 | BST2 | 10.343 |
| 204533_at | chemokine (C-X-C motif) ligand 10 | CXCL10 | 10.319 |
| 218986_s_at | hypothetical protein FLJ20035 | FLJ20035 | 8.787 |
| 203153_at | interferon-induced protein with tetratricopeptide repeats 1 | IFIT1 | 8.606 |
| 205483_s_at | interferon, alpha-inducible protein | G1P2 | 8.500 |
| 214453_s_at | interferon-induced protein 44 | IFI44 | 8.102 |
| 219352_at | hect domain and RCC1-like domain 6 | HERC6 | 7.315 |
| 205569_at | lysosomal-associated membrane protein 3 | LAMP3 | 7.084 |
| 204747_at | interferon-induced protein with tetratricopeptide repeats | IFIT3 | 6.479 |
| 202086_at | interferon-inducible protein p78 | MX1 | 6.204 |
| 213194_at | roundabout, axon guidance receptor, homolog 1 | ROBO1 | 5.562 |
| 202411_at | interferon, alpha-inducible protein 27 | IFI27 | 5.425 |
| 219211_at | ubiquitin-specific protease 18 | USP18 | 4.730 |
| 209417_s_at | interferon-induced protein 35 | IFI35 | 4.528 |
| 205552_s_at | 2',5'-oligoadenylate synthase 1, 40/46 kDa | OAS1 | 4.506 |
| 201601_x_at | interferon induced transmembrane protein 1 (9-27) | IFITM1 | 4.298 |
| 205660_at | 2'-5'-oligoadenylate synthetase-like | OASL | 4.279 |
| 202145_at | lymphocyte antigen 6 complex, locus E | LY6E | 4.124 |
| 204994_at | myxovirus resistance 2 | MX2 | 3.990 |
| 218400_at | 2'-5'-oligoadenylate synthetase 3, 100 kDa | OAS3 | 3.624 |
| 202446_s_at | phospholipid scramblase 1 | PLSCR1 | 3.498 |
| 205829_at | hydroxysteroid (17-beta) dehydrogenase 1 | HSD17B1 | 3.428 |
| 204415_at | interferon, alpha-inducible protein | G1P3 | 3.401 |
| 203148_s_at | tripartite motif-containing 14 | TRIM14 | 3.270 |
| 208436_s_at | interferon regulatory factor 7 | IRF7 | 3.254 |
| 204470_at | chemokine (C-X-C motif) ligand 1 | CXCL1 | 3.093 |
| 211529_x_at | major histocompatibility complex, class I, G | HLA-G | 2.683 |
| 209301_at | carbonic anhydrase II | CA2 | 2.655 |
| 201110_s_at | thrombospondin 1 | THBS1 | 2.496 |
| 201150_s_at | tissue inhibitor of metalloproteinase 3 | TIMP3 | 2.419 |
| 213294_at | hypothetical protein FLJ38348 | FLJ38348 | 2.401 |
| 208729_x_at | major histocompatibility complex, class I, B | HLA-B | 2.377 |
| 200887_s_at | signal transducer and activator of transcription 1 | STAT1 | 2.370 |
| 200923_at | lectin | LGALS3BP | 2.226 |
| 204417_at | galactosylceramidase | GALC | 2.190 |
| 205899_at | cyclin A1 | CCNA1 | 2.172 |
| 200798_x_at | myeloid cell leukemia sequence 1 (BCL2-related) | MCL1 | 2.146 |
| 208282_x_at | deleted in azoospermia | DAZ1 | 2.138 |
| 206376_at | solute carrier family 6 | SLC6A15 | 2.102 |
| 218669_at | RAP2C, member of RAS oncogene family | RAP2C | 0.520 |
| 212463_at | CD59 | CD59 | 0.516 |
| 214657_s_at | trophoblast-derived noncoding RNA | TncRNA | 0.505 |
| 215239_x_at | zinc finger protein 273 | ZNF273 | 0.463 |
| 201893_x_at | decorin | DCN | 0.415 |
| 204614_at | serine (or cysteine) proteinase inhibitor | SERPINB2 | 0.358 |
| 205623_at | aldehyde dehydrogenase 3 family | ALDH3A1 | 0.325 |

TABLE 1-continued

IRDS Gene Signature.

| ID | NAME | Symbol | R nu61/ scc61 |
|---|---|---|---|
| 204019_s_at | likely ortholog of mouse Sh3 domain YSC-like 1 | SH3YL1 | 0.218 |
| 202409_at | putative insulin-like growth factor II associated protein | IGF2 | 0.046 | expression in the radioresistant cell line, and other genes exhibiting decreased expression in the radioresistant cell line. Component genes (e.g., STAT-1) were functionally tested in the mouse system to confirm that IRDS genes mediate the resistance phenotype.

However, because the radioresistant cell line (Nu61) was developed by repeated irradiation and passage of a human squamous cell carcinoma SCC-61 in mouse xenograft and cell culture, it was not known whether differential expression of IRDS genes and radiation resistance resulted from serial irradiation and passage of the tumor cells, or whether differential expression of IRDS genes and radiation resistance were inherent in a subset of tumor cells. Therefore, it was not known whether differential IRDS expression occurred in human primary tumors, whether differential expression of IRDS genes had any clinical relevance, or whether it was a phenomenon unique to the Nu61 cell line.

As detailed below, it was discovered that differential IRDS gene expression occurs in a subgroup of every tumor type tested and that IRDS gene expression is clinically relevant, i.e., differential IRDS gene expression correlates with tumor resistance to chemotherapy and radiation therapy and with reduced survival, increased metastasis, and tumor recurrence. These results indicate that IRDS expression is a useful prognostic or predictive marker for cancer.

As described below in the examples, increased expression of certain IRDS genes (i.e., upregulated IRDS genes) and decreased expression of other IRDS genes (i.e., downregulated IRDS genes) occurs in a subgroup of primary tumors (i.e., IRDS(+) tumors) in each of several different patient populations. Based on analysis of DNA microarray databases from a variety of human cancers, including breast, lung, head and neck, high grade glioma and gastric cancers, tumors were assigned to one of two major cohorts, IRDS(+) and IRDS(−), depending on expression levels of the IRDS gene signature in tumor cells.

Based on retrospective studies of breast cancer tumors in a population of patients for which medical histories are available, IRDS gene signature expression was found to correlate with response to adjuvant chemotherapy and adjuvant radiation therapy. Specifically, patients having IRDS(+) tumors who received adjunctive chemotherapy or radiation therapy exhibited resistance to chemotherapy and radiation. Therefore, the IRDS markers are expected to have value as a therapy predictive marker for the efficacy of adjuvant chemotherapy and radiation therapy in the treatment of cancers.

Additionally, the IRDS gene signature expression has prognostic value. In the examples below, increased expression of certain IRDS genes in high grade gliomas and breast cancer was found to correlate with decreased survival. In breast cancer patients, IRDS expression was found to correlate with risk of metastasis, local-regional failure and recurrence rate.

In contrast to other genomic classifiers, the IRDS gene signature was experimentally selected, and its predictive and prognostic ability appears to be related to its underlying biology. In other words, increased expression of IRDS genes appears to affect outcome. Of the numerous types of human cancers tested, every type was found to have a subgroup that exhibits increased expression of IRDS genes. For this reason, and because there is a mechanistic basis for the predictive value of IRDS, it is reasonably expected that IRDS expression levels may be used as a prognostic or predictive marker for any cancer having an IRDS(+) subpopulation.

Tumors may be classified as IRDS(+) and IRDS(−) by assessing the expression levels of at least one of the IRDS genes listed in Table 1 in any combination, or in combination with any other prognostic marker. Preferably, expression levels of 2, 3, 4, 5, 6, 7 or more of the IRDS genes are assessed. It is envisioned that, in addition to the IRDS genes specifically listed in Table 1, IRDS genes may be expanded to include other interferon pathway genes having increased or decreased expression in radioresistant or DNA damage resistant tumors. It is well within the ability of one skilled in the art, using the teachings provided herein, to identify additional IRDS genes having prognostic or predictive value.

Expression of the IRDS markers may be evaluated by any suitable means. For example, expression may be evaluated using DNA microarrays. Alternatively, RNA transcripts may be measured using real time PCR, or protein products may be detected using suitable antibodies. Methods of determining expression levels of genes by these and other methods are known in the art.

Expression levels of an IRDS gene may be determined by comparison to a suitable reference. For example, as explained in the detailed examples below, IRDS expression levels may be assessed relative to the NU61 cell line. Alternatively, the relative expression level of an IRDS gene in a particular tumor may be determined with reference the expression levels of the same IRDS gene in a number of tumors of the same general class (e.g., breast cancer tumors or high grade gliomas). If the expression level of IRDS genes is greater or less than that of the reference, e.g. Nu61 cell line or the average expression level of tumors of a particular type, IRDS expression may be said to be "increased" or "decreased", respectively. Analytical methods for classifying IRDS expression, determining IRDS status, and IRDS scoring are explained in greater detail below.

In one set of examples, IRDS expression levels were evaluated using by k-means clustering and comparison of the fold change between mean IRDS expression profiles (IRDS centroid) for each group with the cell line data to yield an IRDS class assignment and Pearson correlations. The group of patients with a positively correlated centroid was defined as IRDS(+), and the negatively correlated group was defined as IRDS(−). In other examples, the support vector machine (SVM) (Cortes, C. et al., Machine Learning, 20:273-97 (1995), incorporated herein by reference) and top scoring pairs (TSP) (Tan, A. C. et al., Bioinformatics, 21:3896-904 (2005); Xu, L. et al., Bioinformatics, 21:3905-11 (2005), incorporated herein by reference) classifiers were trained and each used to assign IRDS status to new samples.

It is envisioned that the invention may be practiced using any suitable classifier to determine IRDS status. The classifier may be based on any appropriate pattern recognition method that receives input comprising the IRDS gene profile and provides an output comprising data that indicates status. Because clinical data was not used to model IRDS class membership, these procedures do not bias analysis of clinical outcome using IRDS status as a factor.

The IRDS status may be determined by calculating an IRDS score, which relates to the expression level of IRDS markers. In the examples below, the TSP classifier was used to determine both IRDS status, i.e., IRDS(+) or IRDS(−), and an IRDS score to relate to IRDS status.

For example, for breast cancer patients, the TSP can be restricted to the 49 IRDS genes along with the Perou's "intrinsic" breast cancer genes (Sorlie, T. et al., PNAS, 100: 841-823 (2003)) to analyze gene pairs. Using the gene pairs, an IRDS status of IRDS(+) or IRDS(−) could be determined. An IRDS TSP score was also developed using seven gene pairs by TSP, including seven IRDS genes (STAT1, IF144, IFIT3, OAS1, IFIT1, GIP2, and MX1), the expression of which is increased in IRDS(+) tumors. Although seven specific gene pairs were used in these examples, it is envisioned that any other suitable gene pairs may be used provided one member of each gene pair is an IRDS gene. It is specifically envisioned that the invention may be practiced using more or fewer than seven gene pairs. It is envisioned that other classifier methods known by a person skilled in the art may be used to determine the IRDS status or score.

Applicants envision that any of the genes listed in Table 1 above may be used in the methods of the invention either alone or in combination with any other IRDS gene or other prognostic marker. Although information concerning the expression of as few as one gene is expected to provide useful information, confidence in the accuracy of the classification of a tumor as IRDS(+) or IRDS(−) will increase when more markers are included. Tumors may be analyzed with respect to the expression of groups of IRDS genes, including from 1 to 49 of the genes listed in Table 1, in any combination. It is well within the ability of one of skill in the art to select IRDS genes for analysis from among the genes listed in Table 1.

In the interest of brevity, Applicants are not expressly listing every possible combination of genes suitable for use in the invention. Nevertheless, it should be understood that every such combination is contemplated and is within the scope of the invention. It is specifically envisioned that any combination of IRDS genes that were found to be differentially expressed in the primary tumors may be particularly useful for analysis.

Figure 10:
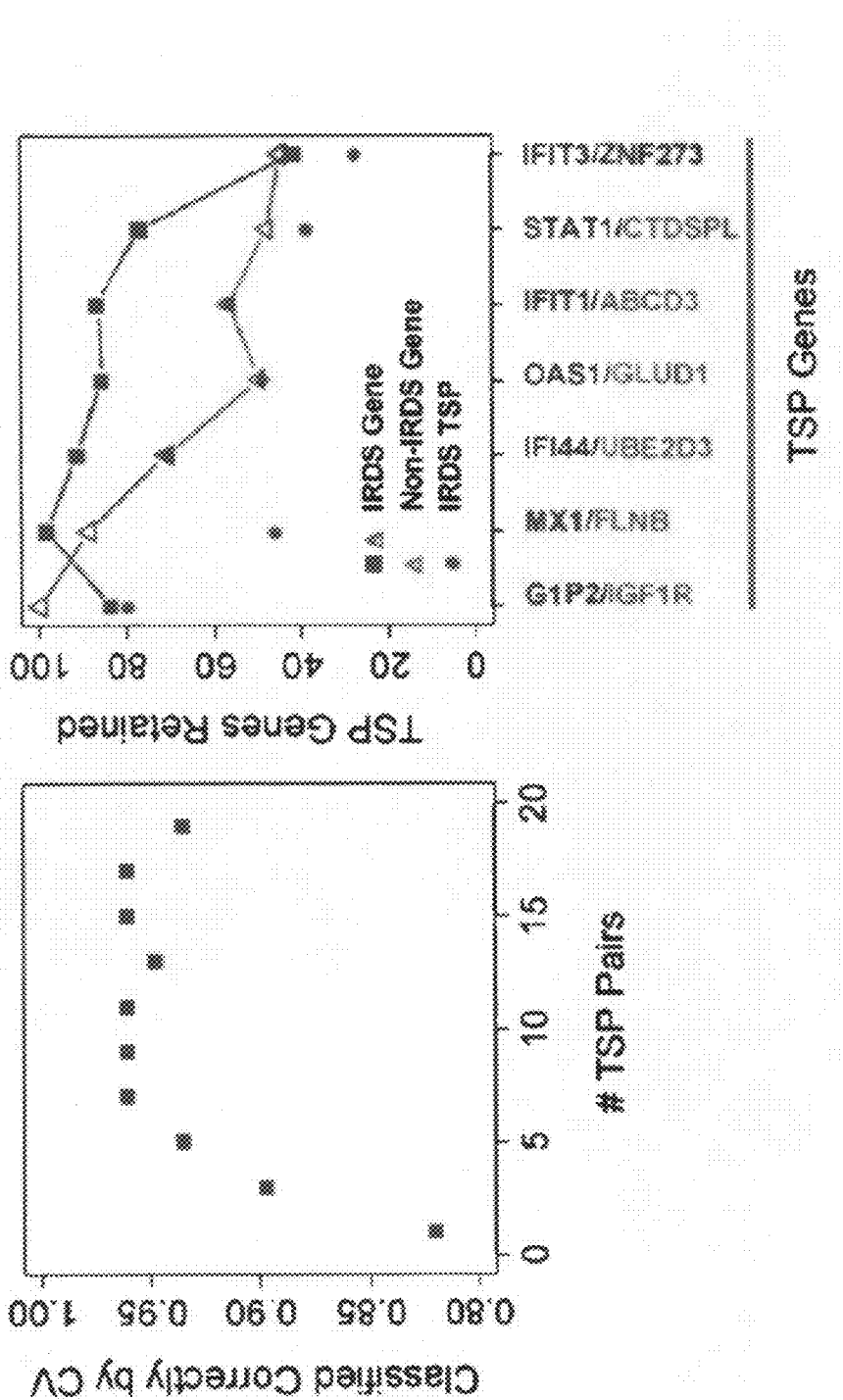
FIG. 10A shows the percent classified correctly for each number pair tested for training of the TSP IRDS classifier.
FIG. 10B shows the proportion of IRDS genes and/or non-genes from each pair retained from the perturbed data over 100 runs.

As seen in FIG. 10, using the TSP method, even one gene pair is able to correctly classify the tumor by IRDS status, as determined by cross validation analysis, suggesting that even one gene pair may be useful to determine IRDS status. This may be particularly true in applications in which IRDS status is used in conjunction with other prognosis markers, such as age, lymph node status, tumor size, distant metastasis and the like.

Although the examples below employ relative expression levels of paired genes to evaluate IRDS status, it is envisioned that one could measure absolute IRDS gene expression levels and determine the IRDS status by comparing absolute expression levels with that of a population of tumors.

The present invention allows tumors to be characterized using the clinically relevant IRDS markers. A tumor from a patient may be characterized by detecting expression of at least one IRDS marker by the tumor. Suitably, the expression of the IRDS marker is used to determine tumor IRDS status, i.e., IRDS(+) or IRDS(−), or to assign an IRDS TSP score. The characterization of the tumor by IRDS status or IRDS TSP score can be used to predict the outcome of cancer treatment, with IRDS(+) status or relatively high IRDS TSP scores being indicative of resistance to chemotherapy and radiation. Additionally, the IRDS status or IRDS TSP score can be used as a prognostic indicator of clinical outcome.

Suitably, tumors can be characterized with respect to IRDS status alone, or in with respect to IRDS status in combination with additional prognostic factors. A "prognostic factor" is a factor that provides information concerning the risk of disease progression. Prognosis factors include, but are not limited to, standard prognostic factors, such as age, tumor size, nodal status, and tumor grade, NKI70 (70 gene signature from Netherlands Cancer Institute) (van de Vijver, M. J. et al., New England Journal of Medicine, 347:1999-2009 (2002); van't Veer, L. J. et al., Nature, 415:530-6 (2002, incorporated herein by reference), lung metastatic markers (Minn, A. J. et al., Nature, 436:518-524 (2005)), and the Oncotype DX recurrence score (RS) (Paik, S. et al., New England Journal of Medicine, 351: 2817-2826 (2004)).

In one embodiment, the invention provides a method for predicting tumor response to a chemotherapeutic agent or radiation by evaluating expression of at least one marker of IRDS by the tumor. The expression of the marker is predictive of tumor response to the chemotherapeutic agent or radiation. Altered expression (i.e., increased or decreased expression) of the IRDS marker by the tumor relative to a reference, consistent with IRDS(+) status, indicates that the tumor may be resistant to the chemotherapeutic agent or radiation, whereas the absence of altered expression relative to the reference consistent with IRDS(−) status indicates that the tumor is likely to be sensitive to the chemotherapeutic agent or radiation.

"Tumor response" as described herein may include, but is not limited to, one or more of: inhibiting growth of the tumor, i.e., arresting or slowing its growth; preventing spread of the tumor, i.e., preventing metastases; causing regression of the cancer; and preventing recurrence of the tumor.

Based on retrospective studies of breast cancer tumors in a population of patients for which medical histories are available, IRDS gene signature expression was found to correlate with response to adjuvant chemotherapy and radiation therapy. Specifically, patients having IRDS(+) tumors who received adjuvant chemotherapy or radiation therapy exhibited resistance to adjunctive therapy. Therefore, the IRDS markers are expected to have value as a therapy predictive marker for the administration of adjuvant chemotherapy and radiation therapy in the treatment of cancers.

The examples below show that IRDS expression may be used to predict response to DNA damaging agents or radiation. It is specifically envisioned that IRDS expression may be used to predict response to chemotherapeutic agents in addition to DNA damaging agents, particularly those that act by stimulating the interferon pathway. A "chemotherapeutic agent," as used herein, refers to any agent that may be used to treat cancer, including, for example, agents that interfere with cell division or with DNA synthesis or function. Chemotherapeutic agents include DNA damaging agents, which may be any agent that causes DNA damage, or interferes with the DNA synthesis or with the DNA damage response of the cell, whether directly or indirectly, including, but not limited to, alkylating agents, e.g., busufan, cisplatin, ifosfamide, or nitrosoureas, e.g. streptozocin, lomustine, and taxol. Chemotherapeutic agents may also include direct or indirect modulators of the interferon pathway, for example, stimulators of the interferon pathway. Interferon pathway stimulators include, but are not limited to, agents such as IFN-α or other chemotherapeutic agents, for example 5-fluoroauracil (5-FU) and others, which stimulate the activation of the interferon pathway. The IRDS status may also be useful for predicting response to immunomodulatory agents including but not limited to TNF, TRAIL, fas, and fas ligand. Additionally, IRDS status may predict response of breast cancer patients to trastuzumab.

Additionally, the methods may be used to predict response to radiation therapy, including radiation treatment that is electromagnetic or particulate in nature. Electromagnetic radiation includes, but is not limited to, x-rays and gamma rays. Particulate radiation includes, but is not limited to, electron beams, proton beans, neutron beams, alpha particles, and negative pimesons.

The term "tumor" is used herein to describe an abnormal mass or growth of cells or tissue that is characterized by uncontrolled cell division. Tumors may be benign (not cancerous) or malignant (cancerous). Tumors may be solid, i.e. from solid organs such as the breast, lung, or head and neck, or non-solid, i.e. from blood, bone marrow, or lymphatic system such as leukemias or lymphomas. Tumors may be identified, monitored or assessed through clinical screening or diagnostic procedures, including, but not limited to, palpation, biopsy, cell proliferation index, endoscopy, mammography, digital mammography, ultrasonography, computed tomography (CT), magnetic resonance imaging (MRI), positron emission tomography (PET), radiography, radionuclide evaluation, CT- or MRI-guided aspiration cytology, and imaging-guided needle biopsy, among others. Such diagnostic techniques are well known to those skilled in the art.

The present invention may be used to predict tumor response of mammalian cancers, especially human cancers, to chemotherapy or radiation, including, but not limited to, lung cancer, prostate cancer, testicular cancer, brain cancer, skin cancer, colon cancer, rectal cancer, gastric cancer, esophageal cancer, tracheal cancer, head and neck cancer, pancreatic cancer, liver cancer, breast cancer, ovarian cancer, lymphoid cancer, leukemia, cervical cancer, vulvar cancer, melanoma, renal cancer, bladder cancer, thyroid cancer, bone cancers or soft tissue cancers.

Additionally, the IRDS gene signature expression has prognostic value. The term prognosis, as used herein, refers to the prediction of cancer attributable progression. Prognosis includes, but is not limited to the survival rate and risk of recurrence, metastatic spread, treatment resistance, and local-regional failure. In the examples below, increased IRDS expression in high grade gliomas and breast cancer was found to correlate with decreased survival. In breast cancer patients, the IRDS expression was found to correlate with the risk of metastasis, local-regional failure, and recurrence rate.

The IRDS status or score of a tumor may be used clinically as both a predictive and prognostic marker to provide information concerning the appropriate treatment modalities and likely treatment outcome. The IRDS may be used in conjunction with other prognostic factors to allow a clinician to predict the outcome of cancer treatment. As seen in the examples, analysis reveals that standard prognostic factors, the NKI70 gene signature and the TSP IRDS score all show a correlation with metastasis-free survival among breast cancer patients treated with adjuvant therapy. When the TSP IRDS score analysis is added to standard prognostic markers analysis, predictive accuracy is improved. Predictive accuracy can be further improved by addition of the NKI70 gene signature. IRDS status can also be predictive of local-regional failure, as seen in the examples for breast cancer. The examples demonstrate improved predictive accuracy of local-regional failure when the IRDS status is used in conjunction with standard prognosis factors or NKI70 gene signature analysis.

In the examples shown below, the methods of this invention use a classifier for predicting prognosis. The classifier can be based on any appropriate pattern recognition method that receives input comprising the IRDS gene profile and provides an output comprising data that indicates a prognosis. The classifier will be trained with training data from a training population of the specific type of cancer being studied where outcomes are known. Thus the IRDS status of the patients can be correlated to their prognosis, and this in turn can be used to classify new samples from patients. Examples are given below using a TSP classifier to correlate IRDS status and prognosis.

The stratification of patients based on their IRDS status may be used to determine a treatment protocol for the patients. For example, patients may be divided into those who have a low risk for metastasis and can be spared adjuvant therapy, those with high risk for metastasis who are likely to benefit from standard treatment, and those with a high risk for metastasis and who are resistant to standard treatment. This stratification permits tailoring of patient treatment protocols to the individual. For example, IRDS(−) tumors are likely to respond to adjunctive chemotherapy and radiation therapy, and treatment can be administered accordingly. Conversely, IRDS(+) tumors are likely to be resistant to adjunctive chemotherapy and radiation therapy, and patients with IRDS(+) tumors can be spared the adverse side effects of a treatment that is unlikely to be beneficial. Tailoring treatment to the patient based on IRDS status will likely result in cost savings, by eliminating administration of ineffective treatments.

It is envisioned that IRDS status can be used to determine long-term care and monitoring protocols for patients, including, but not limited to, determination of follow up appointments and treatments, and screening schedules. Patients having IRDS(+) tumors associated with increased risk of metastasis would ideally have increased surveillance for tumor recurrence or metastasis.

In further embodiments, the relative survival rate of a patient can be predicted by determining the expression of at least one IRDS marker by a tumor sample derived from the patient. Survival in cancer patients is often quantified as a relative cancer survival rate. The relative cancer survival rate is the percentage of patients who survive a certain type of cancer for a specified amount of time. Cancer survival rates are often given in 5, 10 or 20 year survival rates. For instance, the 5-year survival rate for prostate cancer is 99%, which means that of all men diagnosed with prostate cancer, 99 out of 100 lived five years after diagnosis. As seen in the examples below, IRDS status can predict survival rate of patients with high grade glioma and breast cancer, with patients with IRDS (−) tumors living longer than those with IRDS(+) tumors. It is envisioned that a similar phenomenon will be observed in other types of cancers, and that IRDS status can be used to predict survival of patients having other types of cancer, including, but not limited to, lung cancer, prostate cancer, head and neck cancers, testicular cancer, brain cancer, skin cancer, colon cancer, rectal cancer, esophageal cancer, tracheal cancer, pancreatic cancer, liver cancer, breast cancer, ovarian cancer, lymphoid cancer, leukemia, cervical cancer, vulvar cancer, melanoma, renal cancer, bladder cancer, thyroid cancer, bone cancers or soft tissue cancers, and gastric cancers.

Conveniently, IRDS expression may be evaluated using a kit comprising at least one probe suitable for detecting one or more IRDS markers. As used herein, a probe may include any molecule capable of detecting an IRDS marker, including, but not limited to, monoclonal and polyclonal antibodies and oligonucleotides. For example, the kit may comprise an antibody specific for an epitope of an IRDS protein encoded by an IRDS gene, an oligonucleotide probe complementary to at least a portion of an IRDS gene or to at least a portion an RNA (e.g., mRNA) encoded by an IRDS gene, or primer pairs suitable for evaluating IRDS gene expression by a polymerase chain reaction (PCR)-based method, such as real time PCR or reverse transcription PCR. Other methodologies for measuring expression of an IRDS marker may include ribonuclease protection assay, S1 nuclease assay, and Northern blot analysis. Optionally, the kits may include instructions for detecting IRDS detection or for performing the methods of the invention.

The kit may comprise a microarray that may be used to determine expression of at least one IRDS marker by a tumor sample and instructions for analyzing the information for use in the methods of the invention. The microarray includes at least one oligonucleotide comprising a sequence of at least one of the IRDS markers from the group of markers listed in Table 1. Suitably, the microarray includes oligonucleotides comprising a sequence of at least three of the IRDS markers from Table 1. Preferably, the microarray includes oligonucleotides comprising a sequence of at least seven of the IRDS markers from Table 1. The term "microarray" refers to an ordered arrangement of hybridizable array elements, e.g. oligonucleotide probes, on a substrate, e.g. glass slide or silica. Suitably, the microarray comprises control probes to allow for detection of expression levels that can be used in TSP classifiers to determine IRDS status.

The invention provides a method for identifying a gene signature marker, the expression of which correlates with clinical outcome. The method includes developing a radiation or chemotherapeutic cell line from a sensitive cell line and identifying genes that differentially expressed between the resistant and sensitive cell lines, the genes thus identified forming a resistance gene signature. The resistance gene signature status can be determined for tumors from a population of humans of known clinical outcomes. The resistance gene signature status can be correlated with clinical outcome, and used to new tumor samples. The examples below describe this procedure for a squamous cell carcinoma derived gene signature that was then used to correlate the gene signature in breast cancer to clinical outcome, but it is envisioned that it can be applied to other tumor cell lines.

EXAMPLES

Example 1

Analysis of IRDS Expression in Primary Human Tumors

As previously described, a 49 IRDS gene signature was identified by evaluating differential gene expression between radiation sensitive (SCC61) and resistant (Nu61) tumor cell lines using the Affymetrix U133A GeneChip (Khodarev, N. et al., PNAS, 101:1714-1719 (1994)). The average signal intensity for each gene was computed from triplicate samples from SCC61 and Nu61 and transformed into log base 2. The difference between SCC61 and Nu61 was calculated, resulting in the IRDS centroid for the cell line data.

Example 2

IRDS Gene Signature is Expressed Across a Variety of Primary Tumors

Expression of the IRDS gene signature in primary tumor samples was compared with that of the experimentally-derived radioresistant tumor cell line signature Nu61. The expression levels of the IRDS gene signature (Table 1) in various human tumor study populations were determined by gene array analysis using methods similar to those described previously (Minn, A. J., et al., Nature, 436:518-524 (2005), incorporated herein by reference). For non-Affymetrix platforms (breast, head and neck), the corresponding probes for each of the 49 IRDS genes were matched based on Gene Symbols and Unigene accession numbers and duplicate probes removed.

The hierarchical clustering of the expression pattern of the 49-gene IRDS gene signature among primary tumors (i.e., head and neck, lung, prostate, breast, and high grade glioma) is shown in FIG. 1A. The clustering used microarray data derived from data sets listed in Table 2. The breast cancer data presented in FIG. 1A was based on the NKI78 data set. Using the IRDS genes, k-means clustering was performed using TIGR MultiExperiment Viewer version 4.0 (Saeed, A. I. et al, Biotechniques, 34:374-8 (2003)) for each of the microarray data sets with k=2 and requiring 90% consensus for each of the two clusters after 500 runs. The average signal intensity for each of the IRDS genes was then averaged for each of the two consensus clusters and the fold change between clusters was calculated, which was then compared to the cell line centroid using a Pearson's product moment correlation coefficient. The cell line centroid was calculated as described in Example 1. For all of the data sets, the correlation coefficient was highly significant (p<0.001). Patients in each consensus cluster for each cancer type were designated IRDS(+) or IRDS(−). With reference to FIG. 1A, the thick line above each dendrogram indicates the tumors that are classified as IRDS (+).

TABLE 2

Microarray data sets used in this study.

| Cancer Type | Alias | # of Samples | References |
|---|---|---|---|
| Breast | NKI 78 | 78 | van't Veer, L. J., et al., Nature, 415: 530-6 (2002) |
| Breast | NKI 295 | 295 | Van de Vijver, M. J., et al., New England Journal of Medicine, 347: 1999-2009 (2002) |
| Breast | Stockholm 159 | 159 | Pawitan, Y., et al, Breast Cancer Research, 7: R953-64 (2005) |

TABLE 2-continued

Microarray data sets used in this study.

| Cancer Type | Alias | # of Samples | References |
|---|---|---|---|
| Breast | Radcliffe 99 | 99 | Sotiriou, C., et al., PNAS, 100: 10393-8 (2003) |
| Breast | Erasmus 286 | 286 | Wang, Y., et al., Lancet, 365: 671-9 (2005) |
| Breast | MGH 60 | 60 | Ma, X. J., et al., Cancer Cell, 5: 607-16 (2004) |
| Head and Neck | | 60 | Chung, C. H., et al., Cancer Cell, 5: 489-500 (2004) |
| Lung | | 86 | Bild, A. H., et al., Nature, 439: 353-7 (2006) |
| Prostate | | 78 | Stephenson, A. J., et al., Cancer, 104: 290-8 (2005) |
| High grade glioma | | 185 | Phillips, H. S., et al., Cancer Cell, 9: 157-73 (2006) |

Distribution of IRDS(+) and IRDS(−) tumors within the populations of head and neck, lung, prostate, breast, and high grade glioma primary tumors was determined by comparing the fold change between the centroids derived from partitioning the microarray data by k-means clustering using the IRDS genes to the fold change between the IRDS(+) and IRDS(−) cell line centroid for all the samples. FIG. 1B shows a heatmap, with each column corresponding to the gene indicated below the heatmap. The Pearson correlation coefficient from a comparison between the primary tumors to the cell line is indicated on the right. By this analysis, the groups of patients with a positively correlated IRDS centroid were defined to be IRDS(+), and the groups of patients with negatively correlated centroid were defined as IRDS(−). For head and neck, lung, prostate, breast, and high grade glioma patients, 37%, 48%, 29%, 46%, and 50% were found to be IRDS(+). Thus, IRDS gene signature is expressed in a substantial subgroup of patients across a variety of cancers.

Example 3

Figure 2:
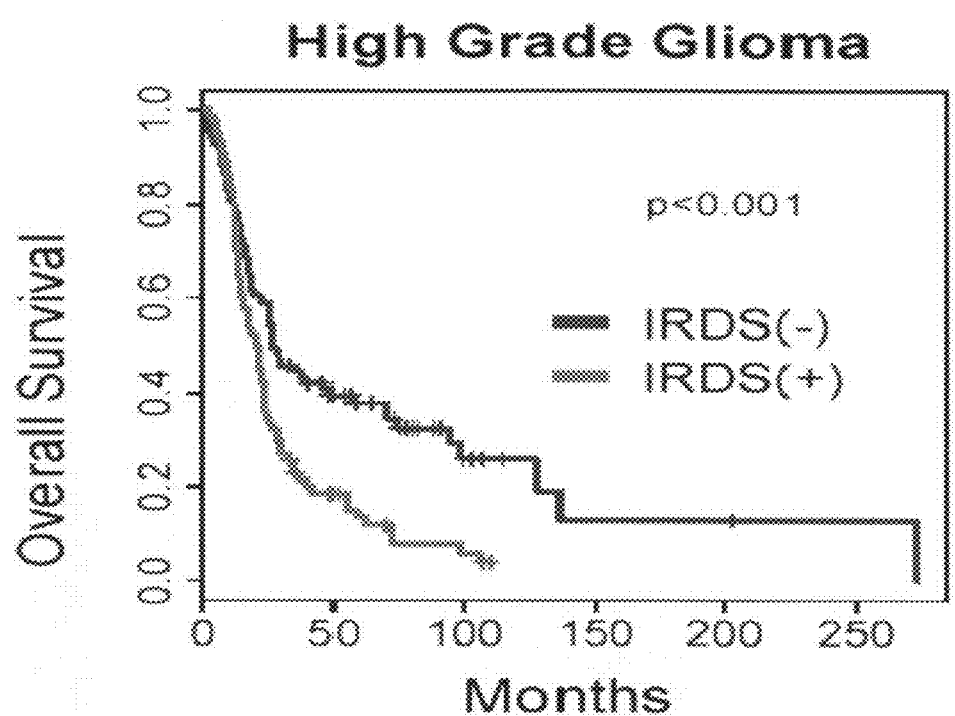
FIG. 2 shows the overall survival curves for IRDS(−) and IRDS(+) patients with high grade glioma.

IRDS Expression Predicts Outcome after Adjuvant Radiation in High Grade Glioma Patients To evaluate whether patients that express the IRDS gene signature demonstrated clinical resistance to DNA damaging agents, overall survival of high grade glioma patients receiving adjuvant radiation was evaluated as a function of IRDS status. Each of the 185 high grade gliomas (Table 2) were classified as IRDS(+) or IRDS(−) as described above. As can be seen from FIG. 2, which shows the fractional survival of patients with grade 3 or 4 gliomas over time, patients with IRDS(+) gliomas have worse overall survival than patients with IRDS(−) tumors ($p < 0.001$). Thus, IRDS expression may confer resistance to adjuvant radiation treatment and shorten median survival for high grade glioma patients, whereas patients with IRDS(−) tumors have a longer survival time.

Example 4

Study Populations Used for Breast Cancer Studies

In some studies, a 295 breast cancer patient cohort was used. Gene expression profiles of tumors from a series of 295 stage I and II breast cancer patients treated at the Netherlands Cancer Institute between 1984 and 1995 was previously reported (van de Vijver, L. J. et al., New England Journal of Medicine, 347:1999-2009 (2002)). The clinical data used for the earlier publications was updated through January 2001. For this study, all patient charts were reviewed and clinical data was updated until Jan. 1, 2005. The median follow up is 10.2 years for all patients and 12 years for patients alive. Distant metastasis was analyzed as first event only. If a patient developed a local recurrence, axillary recurrence, contralateral breast cancer or a second primary cancer (except for non-melanoma skin cancer), she was censored at that time. An ipsilateral supraclavicular recurrence shortly preceded distant metastasis in all but one patient; therefore, these patients were not censored at time of ipsilateral supraclavicular recurrence. There were 161 patients who underwent breast conservation that consisted of adjuvant external beam radiation primarily to 50 Gy (mean 50.2 Gy, range 50-54 Gy) followed by a boost (89% of patients) using photons, electrons, or iridium-192 (mean 18 Gy, range 14-26 Gy). There were 110 patients who received adjuvant chemotherapy which primarily consisted of CMF.

Example 5

IRDS Expression in Breast Cancer Patient Predicts Response to Radiation Therapy

A clinically annotated data set of 295 early stage breast cancer patients (NKI 295), for which detailed clinical information is available, was examined to determine whether there exists a relationship between IRDS status and clinical outcome. Each of the 295 patients was classified as IRDS(+) or IRDS(−) using supervised class prediction methods trained on the 78 breast cancer patient cohort (NKI78) with the k-means-derived IRDS class assignments described in Example 1. Only 49 IRDS genes were used to develop this classifier using the BRB-ArrayTools 3.4.1 and 3.5.0 Beta_1 developed by Dr. Richard Simon and Amy Peng Lam. A support vector machine predictor with a linear kernel and default tuning parameter and misclassification weights was used in this analysis.

Of the 295 patients, 61 were already classified in the NKI78 cohort. Therefore, 235 previously unclassified patients were classified using the support vector machine (SVM) classifier, and the original IRDS status from k-means clustering was used for the 60 overlapping patients (one member of the group of 61 patients was not included due to missing values).

Figure 3:
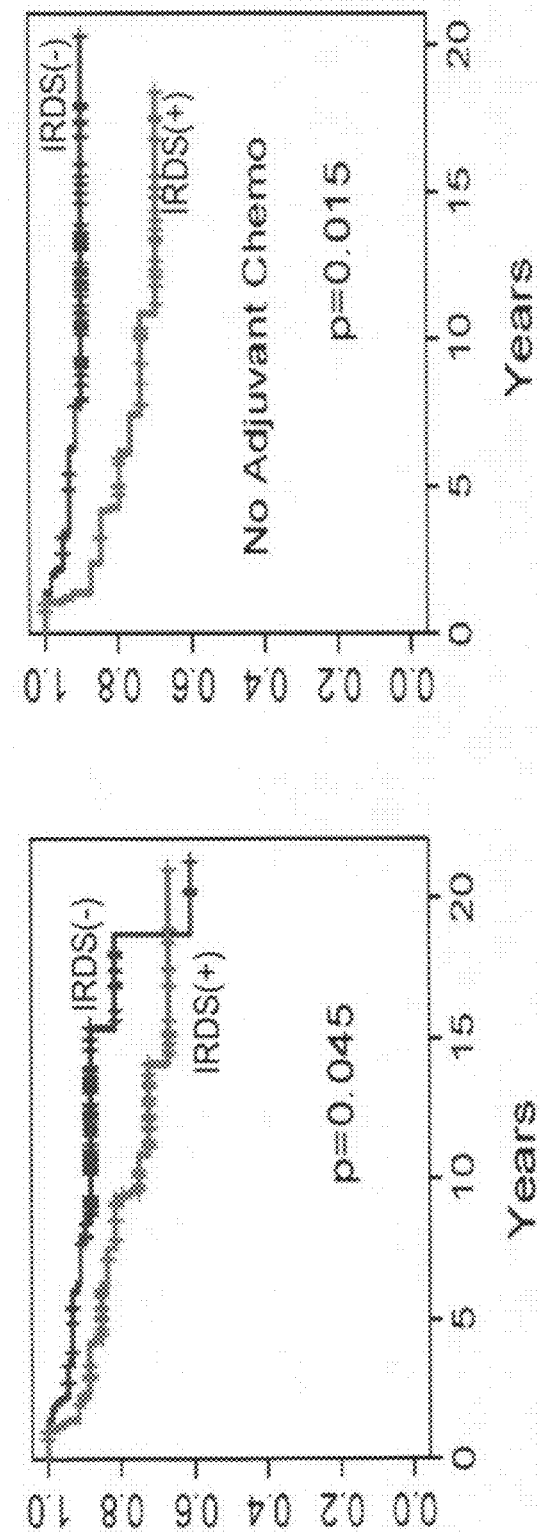
FIG. 3A shows the local-regional control survival curves of IRDS(+) or IRDS(−) breast cancer patients from the NKI295 cohort that received adjuvant chemotherapy.
FIG. 3B shows the local-regional control survival curves of IRDS(+) and IRDS(−) breast cancer patients from the NKI295 cohort that did not receive adjuvant chemotherapy.

A subset of 161 patients of the NKI 295 cohort received breast conservation therapy (excision of the primary tumor and radiation). Local-regional control for these 161 patients was expressed as the percentage of patients without local-regional failure over time as a function of IRDS status (FIG. 3A). IRDS(+) patients were at greater risk for local-regional failure regardless of whether they received adjunctive chemotherapy (FIG. 3B). These results indicate that breast cancer patients having an IRDS(+) tumor may require therapy other than breast conservation therapy, and that they are not likely to respond to adjunctive chemotherapy. Additionally, breast cancer patients having IRDS(−) tumors are better candidates for breast conservation therapy and are more likely to respond to adjuvant chemotherapy.

Example 6

Figure 4:
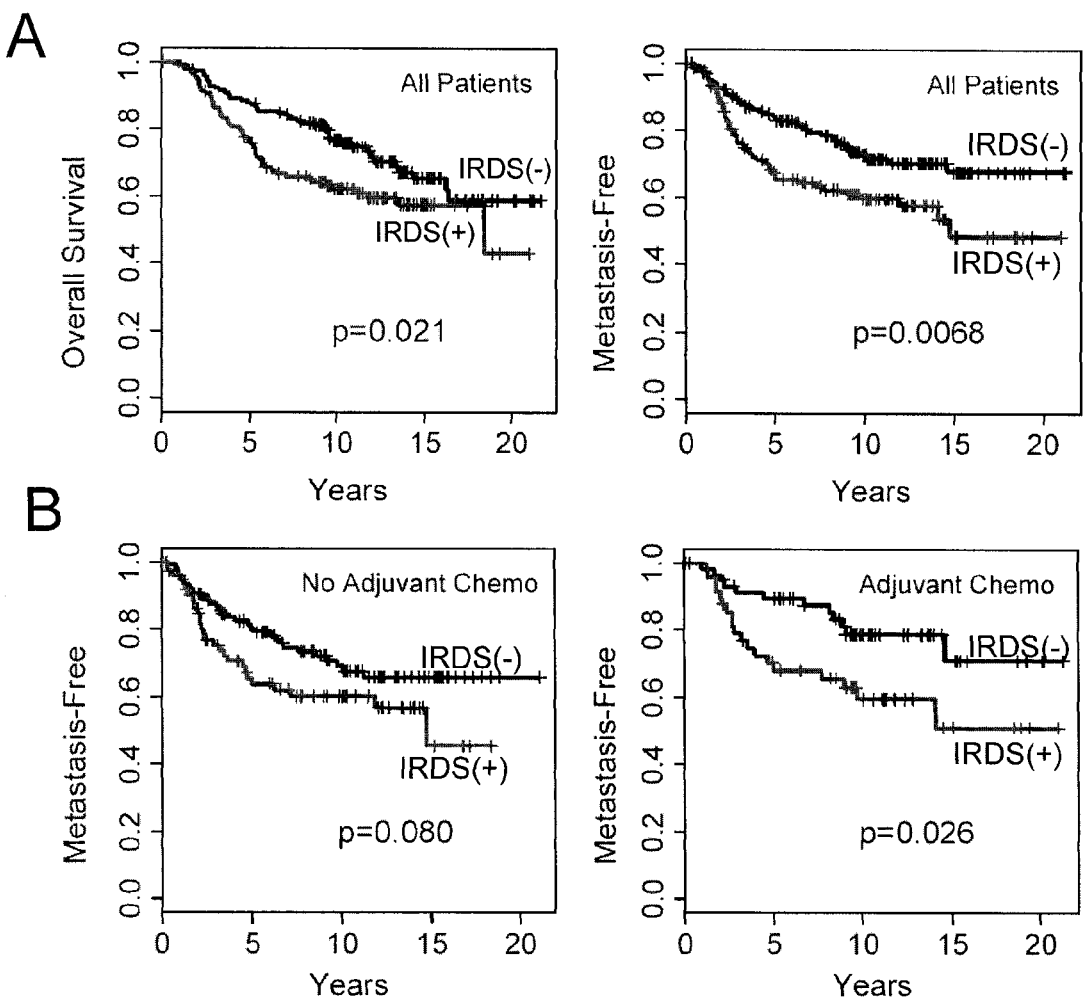
FIG. 4A shows the overall survival curves and the metastasis-free survival curves for the IRDS(+) and IRDS(−) breast cancer patient cohort of the NKI295.
FIG. 4B shows the overall survival curves and the metastasis-free survival curves for the IRDS(+) and IRDS(−) subpopulations of the 110 patients that received adjuvant chemotherapy and 185 patients that did not receive adjuvant chemotherapy from the NKI295 breast cancer cohort.

IRDS Status is Predictive of Overall Survival and Metastasis in Breast Cancer Patients Overall survival and metastasis-free fractions for all IRDS (+) and IRDS(−) breast cancer patients from the NKI295 cohort over time is shown in FIG. 4A. FIG. 4B shows the metastasis-free survival fraction for the IRDS(+) and IRDS (−) subgroups of the 110 patients that received adjuvant chemotherapy (Adjuvant Chemo) and the 185 patients that did not receive adjuvant chemotherapy (No Adjuvant Chemo) from the NKI295 cohort as a function of time. Breast cancer patients having IRDS(−) tumors have better overall survival and reduced incidence of metastasis than patients having IRDS(+) tumors, an effect that is primarily restricted to IRDS (−) patients treated with adjuvant chemotherapy. This was also confirmed by a formal statistical test of interaction between chemotherapy and IRDS status (p=0.05) in a multivariate Cox proportional hazards model that controlled for standard prognostic markers (age, tumor size, number of lymph nodes, estrogen receptor status, histological grade).

For this analysis, overall survival was defined as death by any cause. Survival analysis using the Kaplan-Meier method and the long-rank test was performed using the "survival" package 2.26 in R (Terry Therneau and ported by Thomas Lumley). Cox proportional hazard regression modeling (Simon, R. et al., Journal of Clinical Oncology, 23:7332-41 (2005); Kattan, M. W. et al., Clinical Cancer Research, 10:822-4 (2004); Katz, E. M. et al., National Clinical Practical Oncology, 2:482-3 (2005)) and the test for the proportional hazards assumption of a Cox regression was preformed with the "survival" package.

Example 7

Figure 5:
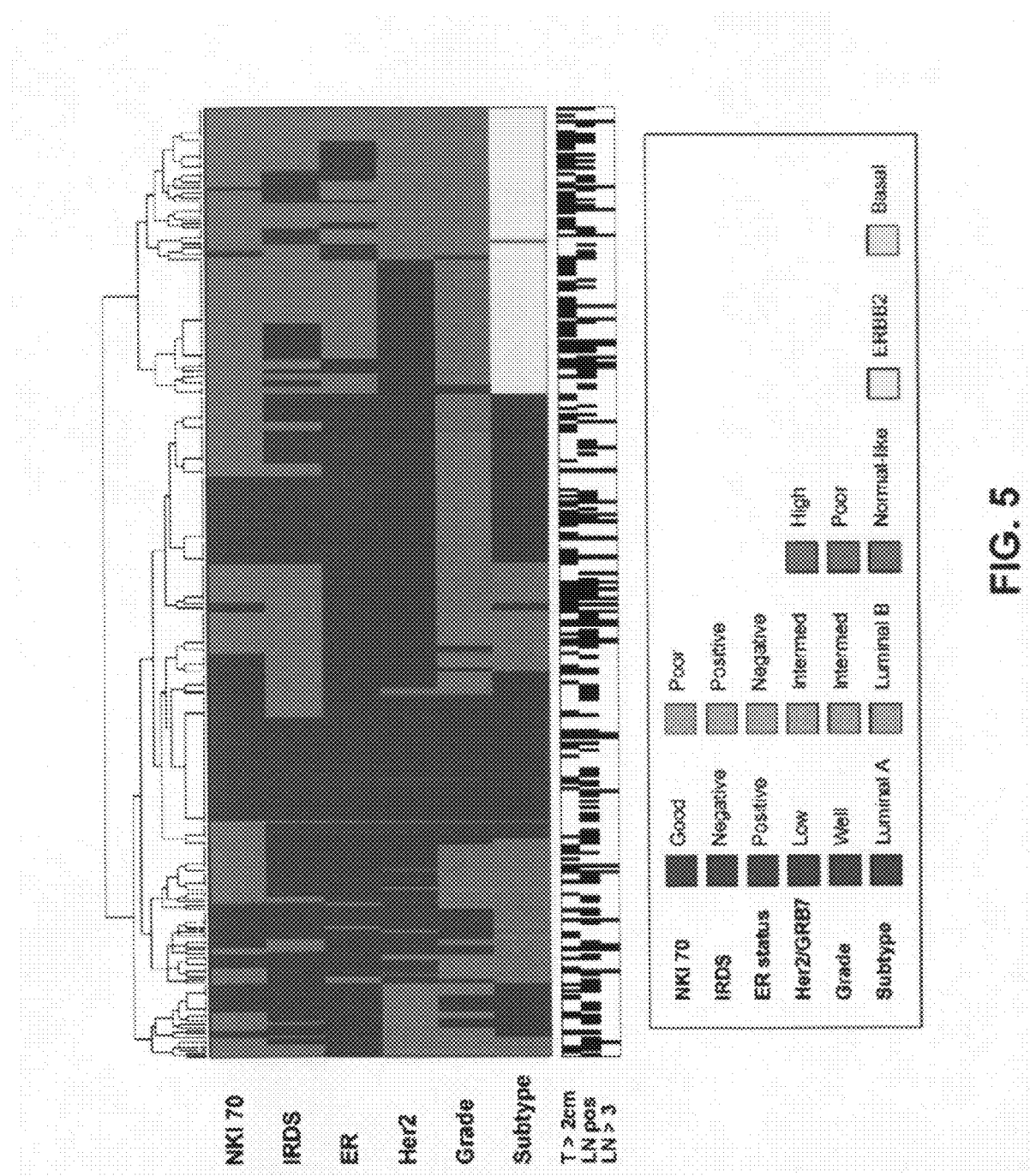
FIG. 5 shows the hierarchical clustering of the NKI295 cohort with the indicated pathological and genomic markers.

Determination of Clinical Information, Prognostic Marker Status, and Risk Stratification The IRDS status of each member of the 295 patient breast cancer cohort was compared to other clinical information and prognostic markers. Most of the clinical and pathological information for the 295 patients has been previously published by Chang et al (Chang, H. et al., PNAS, 102:3738-43 (2005)). Molecular subtype assignments and Oncotype DX recurrence score estimates are from Fan et al (Fan, c. et al., New England Journal of Medicine, 355:560-9 (2006)). Estimation of Her2 amplicon expression using the microarray data was done using the probes for Her2/ERBB2 and GRB7. Hierarchical clustering of clinical, pathological, and genomic markers was performed using the "Heatplus" package 1.2.0 (by Alexander Ploner) for the R language and environment for statistical programming version 2.31 (R Development Core Team, R Foundation for Statistical Xomputing, Bienna, Austria, www.R-project.org). FIG. 5 depicts the relationship between IRDS expression and other prognostic markers using hierarchical clustering. FIG. 5 shows the heat map, where individual patients are represented by columns, and the pathological and genomic markers are in rows. Phenotypic characteristics of the individual patients are separately shown below the heatmap in FIG. 5 (T=tumor, LN=lymph node, pos=positive). IRDS expression tracks with tumor grade and expression of NKI70 poor prognosis signature marker.

Example 8

Figure 6:
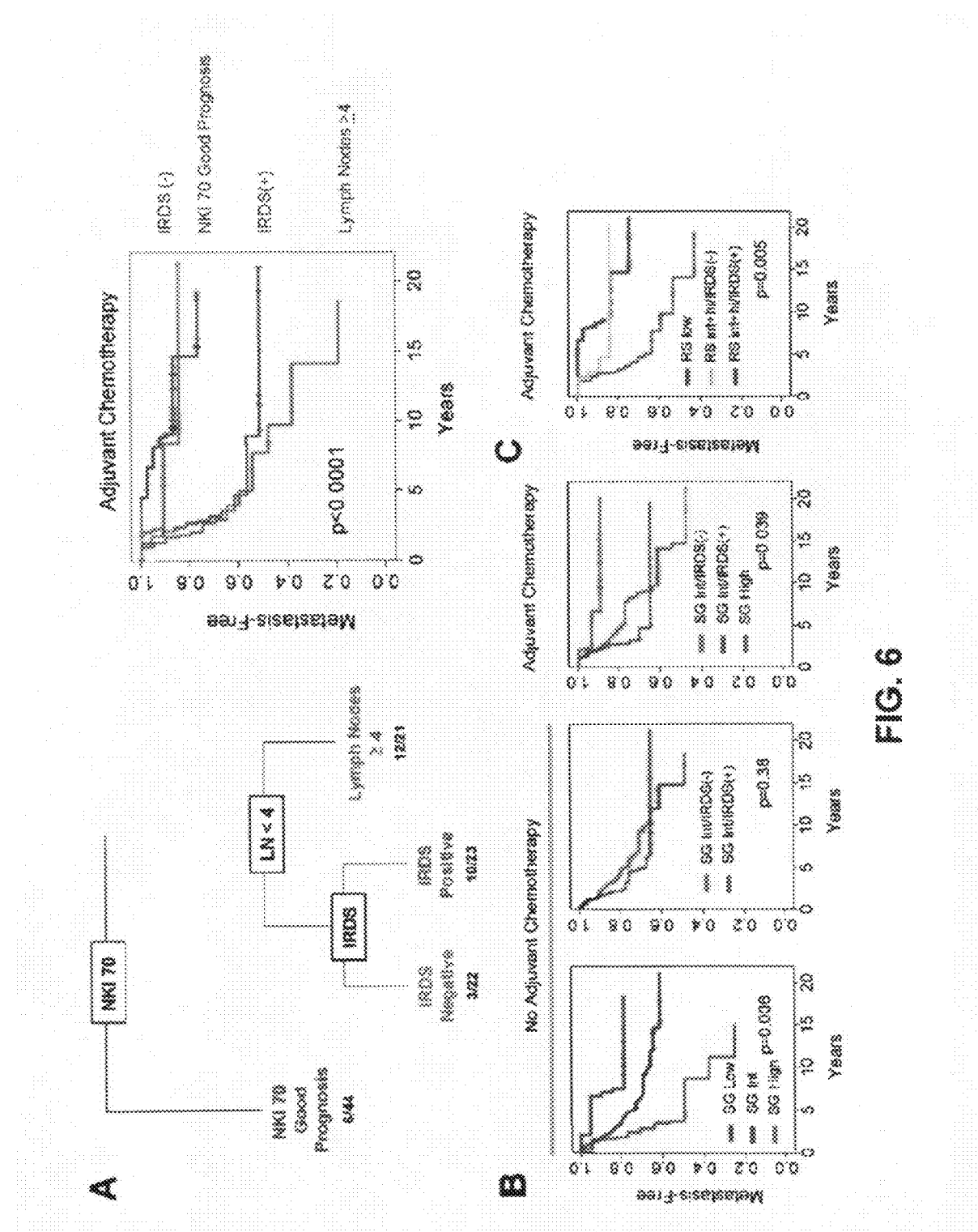
FIG. 6A shows the survival tree to classify patients and metastasis-free survival curves of the 110 patients from the NKI295 breast cancer cohort that received adjuvant chemotherapy.
FIG. 6B shows the metastasis-free survival curves for each group classified by the 2005 St. Gallen consensus criteria (SG) and the metastasis-free survival curves for the intermediate SG subgroup further stratified for IRDS(+) and IRDS(−) status.
FIG. 6C shows the metastasis-free survival curves for the IRDS(−) and IRDS(+) SG intermediate and high risk patients.
FIG. 6D shows the metastasis-free survival curves for the patients treated with adjuvant chemotherapy classified by RS score and IRDS status.

IRDS Expression Predicts Benefit from Adjuvant Chemotherapy Among High Risk Early Stage Breast Cancer Patients To determine if IRDS expression can be used as a therapeutic predictive marker within established risk groups, the metastasis-free survival curves were determined for patients with high risk early stage breast cancer. Recursive partitioning analysis was performed on 110 breast cancer patients from NKI295 that received adjuvant chemotherapy using the "rpart" package 3.1-29 (Terry Therneau and Beth Atkinson and ported by Brian Ripley). The following markers were used to construct the survival tree: tumor size, number of positive lymph nodes, ER status, grade, Her2 over-expression group, NKI70 gene signature, and IRDS status. High risk breast cancer patients had a NKI70 poor prognosis gene signature, and early stage was defined as less than 4 lymph nodes positive. FIG. 6A shows the partitioning tree and the metastasis-free survival for each group shown in the terminal nodes of the partitioning tree (the groups are color coded). Below each node are the number of events per number of observations. Each of the 185 patients of the NKI295 cohort that did not receive adjuvant chemotherapy was assigned to low, intermediate or high risk group based on the 2005 St. Gallen consensus criteria (SG). FIG. 6B shows the metastasis-free survival fraction as a function of time for the SG groups, and the further analysis of the intermediate SG group divided by IRDS status (data representative of the results of all three groups, high, intermediate and low). Each of the 110 patients who received adjuvant chemotherapy was also assigned to a low, intermediate or high risk group based on the SG. The SG intermediate and high risk groups were further stratified by IRDS status (SG low risk only contained one patient). FIG. 6C shows the metastasis-free survival fraction over time for the IRDS(−) and IRDS(+) SG intermediate risk patients, and the unstratified high risk patients (no significant difference was observed after stratifying the SG high risk patients). The p-value shown is for comparison between all three groups. Comparison between SG int/IRDS(−) vs SG int/IRDS(+) gives a p-value of 0.032. The 85 breast cancer patients who received adjuvant therapy from the 225 ER positive patients from the NKI295 cohort were assigned to a low or intermediate/high risk groups according to the Oncotype DX recurrence score (RS). The RS intermediate/high risk group was then further separated based on IRDS status. FIG. 6D shows the metastasis-free survival as a function of time for all patients that received adjuvant chemotherapy. The p value shown is for the comparison between all three groups. Comparison between RS ind+hi/IRDS(−) and RS ind+hi/IRDS(+) gives a p-value of 0.048. No statistical significance was observed between patients who did not receive adjuvant chemotherapy (140 ER positive patients) that were stratified.

IRDS expression predicts benefit from adjuvant chemotherapy in high risk early stage breast cancer patients.

Example 9

A Simple Classifier can be Used to Determine an IRDS Status or Score, and the IRDS Score Correlates with Metastatic Risk in Breast Cancer Patients Treated with Adjuvant Therapy Issues with data normalization and the large number of genes that comprise microarray signatures make it difficult to test complex classifiers either on different microarray platforms or with other assays, such as real-time PCR. To address this issue, top-scoring pairs (TSP) classifier (Tan, A. C., et al., Bioinformatics, 21:3896-904 (2005); Xu, L. et al., Bioinformatics, 21:3905-11 (2005), incorporated herein by reference) was used to classify the NKI295 breast cancer cohort. The TSP method is insensitive to differences in normalization and used simple decision rules based on measuring pair-wise relative expression between limited number of gene pairs. Classifier training was preformed on the NKI78 breast cancer cohort to determine the top seven gene pairs. Using the 78 breast cancer patient cohort, the BRB-ArrayTools 3.5.0 Beta_1 was used to train a TSP classifier for the k-means-derived IRDS class assignments by comparison to the cell line signature. The TSP algorithm selects for gene pairs, necessitating genes besides the 49 IRDS genes. Allowing for a false discovery of only one gene with 99% confidence, there are 162 genes that are differentially expressed between IRDS (+) and IRDS(-) tumors. Although 22 of the 49 IRDS genes are among these 162 genes, even with stringent filtering, the TSP algorithm would likely select gene pairs that did not contain IRDS genes. The TSP algorithm was restricted using the 49 IRDS genes along with the Perou's "intrinsic" breast cancer genes. The intrinsic breast cancer genes are 534 genes used to define the molecular subtypes reported by Perou and colleagues. From their work, these genes were derived from unsupervised class discovery and showed little variation within the same tumor but high variation between different tumors. The intrinsic genes have been shown to discriminate the different subtypes across different microarray studies and platforms. There were 635 intrinsic breast cancer genes on the NKI78 Agilent microarray platform (duplicate probes not removed) which were combined with the 49 IRDS genes and probes with missing values in more than one sample were excluded, leaving 648 genes. Thus the intrinsic genes would be a small set of independent breast cancer genes previously tested across different studies/platforms that could be combined with the IRDS for gene pair selection by the TSP method.

Using patients from the 78 patient cohort as a training set for the TSP classifier, the number of gene pairs was selected by evaluating prediction accuracy using 10-fold cross validation and evaluating an odd number of gene pairs from one to 19 using the class assignments for IRDS status defined by comparison to the cell line signature. A plateau in prediction accuracy at 95% was observed at seven gene pairs as seen in FIG. 10A; therefore, seven gene pairs were selected. Each gene pair contained an IRDS gene with the seventh gene pair containing two IRDS genes. For each gene pair, the probability that the IRDS gene has an expression value greater than the non-IRDS gene is greater for IRDS(+) samples. With gene pair seven where both genes were from the IRDS, the probability that IFIT3 levels are greater than ZNF273 is greater in IRDS(+) samples. A majority vote method was used to train the TSP IRDS classifier, meaning that if four out of seven IRDS genes scored positive, the sample would be classified as IRDS(+). To assess the stability of these seven gene pairs, we added Gaussian noise based on the calculated variance of the training set and ran the TSP algorithm 100 times using seven gene pairs. The data was perturbed by sampling from a normal distribution with mean zero and variance equal to the $25^{th}$ percentile of the calculated variance from the entire data set, and adding this noise to a random sample of 10% of the training set. The $25^{th}$ percentile was chosen rather than the median because a significant proportion of genes were differentially expressed. After 100 runs using the perturbed data sets, the proportion of times each or both of the genes from the seven gene pairs were selected were calculated as seen in FIG. 10B. These results demonstrated that the IRDS is relatively stable and do not significantly fall off until seven gene pairs. The non-IRDS genes are less stable after the third pair as non-IRDS genes from other pairs can be substituted.

Figure 7:
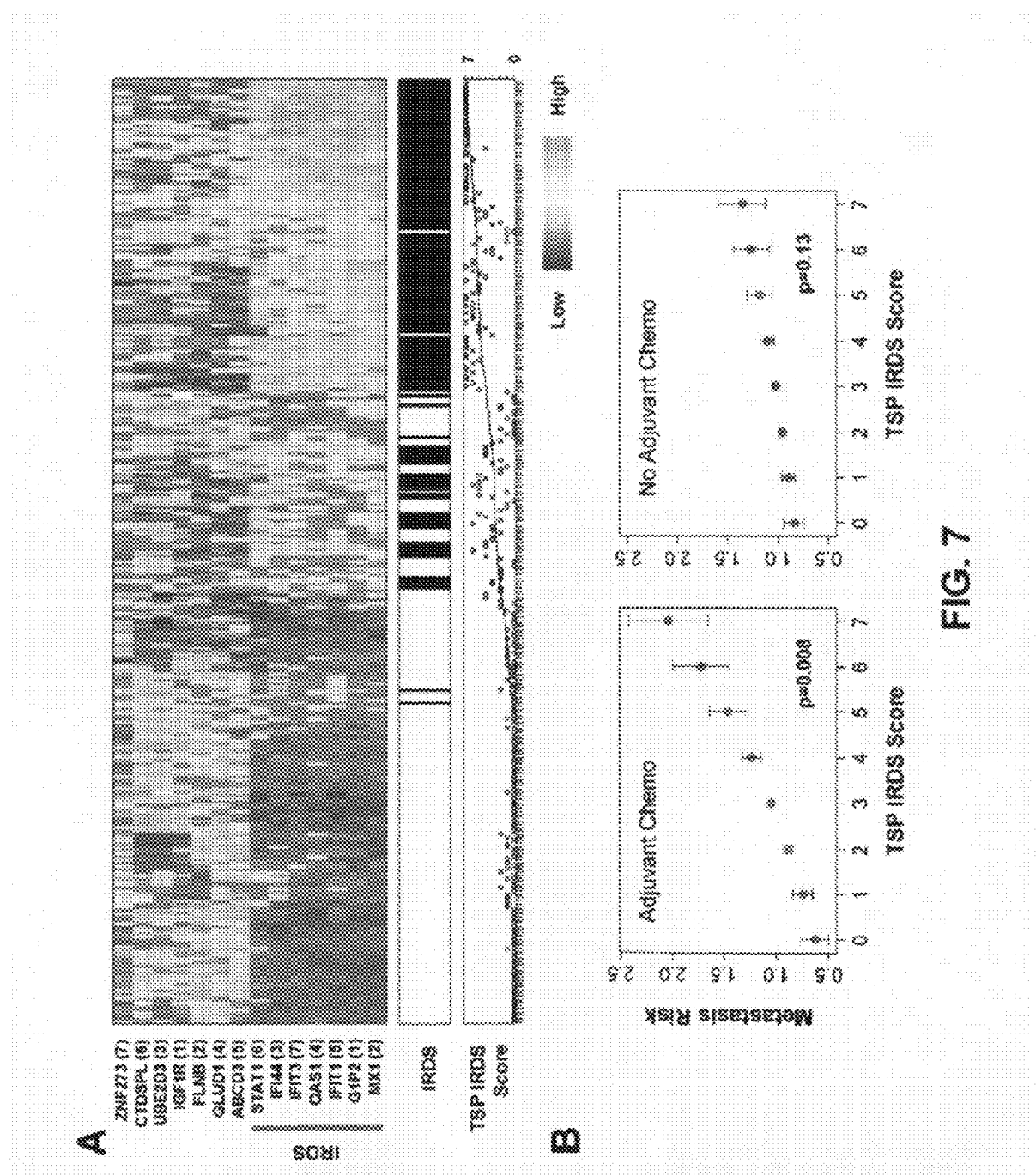
FIG. 7A shows the hierarchical clustering of the NKI295 breast cancer cohort to expression levels of the 7 gene pairs, and the resulting IRDS classification and scores below.
FIG. 7B shows the dot graph relating the TSP IRDS score to metastasis risk with and without adjuvant chemotherapy.

This classifier was then applied to the NKI295 cohort. FIG. 7A shows the heat map demonstrating each gene expression levels, with gene pairs numbered. Each column is a primary tumor and each row is a gene, with light grey representing high expression and dark grey low. The IRDS classification (IRDS(+) (black bar) or IRDS(-) (white bar)) and the number of gene pairs that score with the TSP method are shown below the heatmap for each of the patients in the NKI295 cohort.

The number of gene pairs that scored positive (IRDS TSP Score) was used in a Cox proportional hazards regression model for metastasis-free survival. FIG. 7B shows there was a significant relationship between risk for metastasis and the number of TSP pairs scoring positive in patients that received adjuvant chemotherapy but not in those that did not. Thus, the use of the IRDS score (from 7 gene pairs) was demonstrated to be used to assess risk for breast cancer patients that receive adjuvant therapy. The association of clinical outcome with the TSP classifier determined by majority vote is shown in Example 12.

Example 10

IRDS Status Adds to Predictive Accuracy of Standard and Other Genomic Markers in Predicting Outcomes for Breast Cancer Patients Treated with Adjuvant Chemotherapy An important aspect of developing of a prognostic and therapeutic predictive markers is to evaluate whether inclusion of a new marker enhances predictive accuracy. Random survival forests, which is an ensemble partitioning tree method for censored data that is virtually free of model assumptions, was used to analyze 110 breast cancer patients from the NKI295 cohort treated with adjuvant chemotherapy. The standard and genomic markers used in this study included tumor size, lymph node positive, ER status, grade, age, NKI70 signature and TSP IRDS score. This method involves constructing survival trees from bootstrap samples using randomly selected covariates for tree splitting in order to deliver an ensemble cumulative hazard estimate for metastasis-free survival. Analysis using random survival forests was accomplished using "randomSurvivalForest" package 1.0.0 (Hemant Ishwaran and Udaya B. Kogalur). In general, 1000 survival trees were evaluated, the default "conserve" splitting rule was used, and the default number of predictors was randomly sampled at each split. To estimate prediction accuracy, an out-of-bag Harrell's concordance index was average over 50 runs using standard prognostic markers (age, tumor size, number of positive lymph nodes, grade, ER status) with or without genomic marker(s). FIG.

Figure 8:
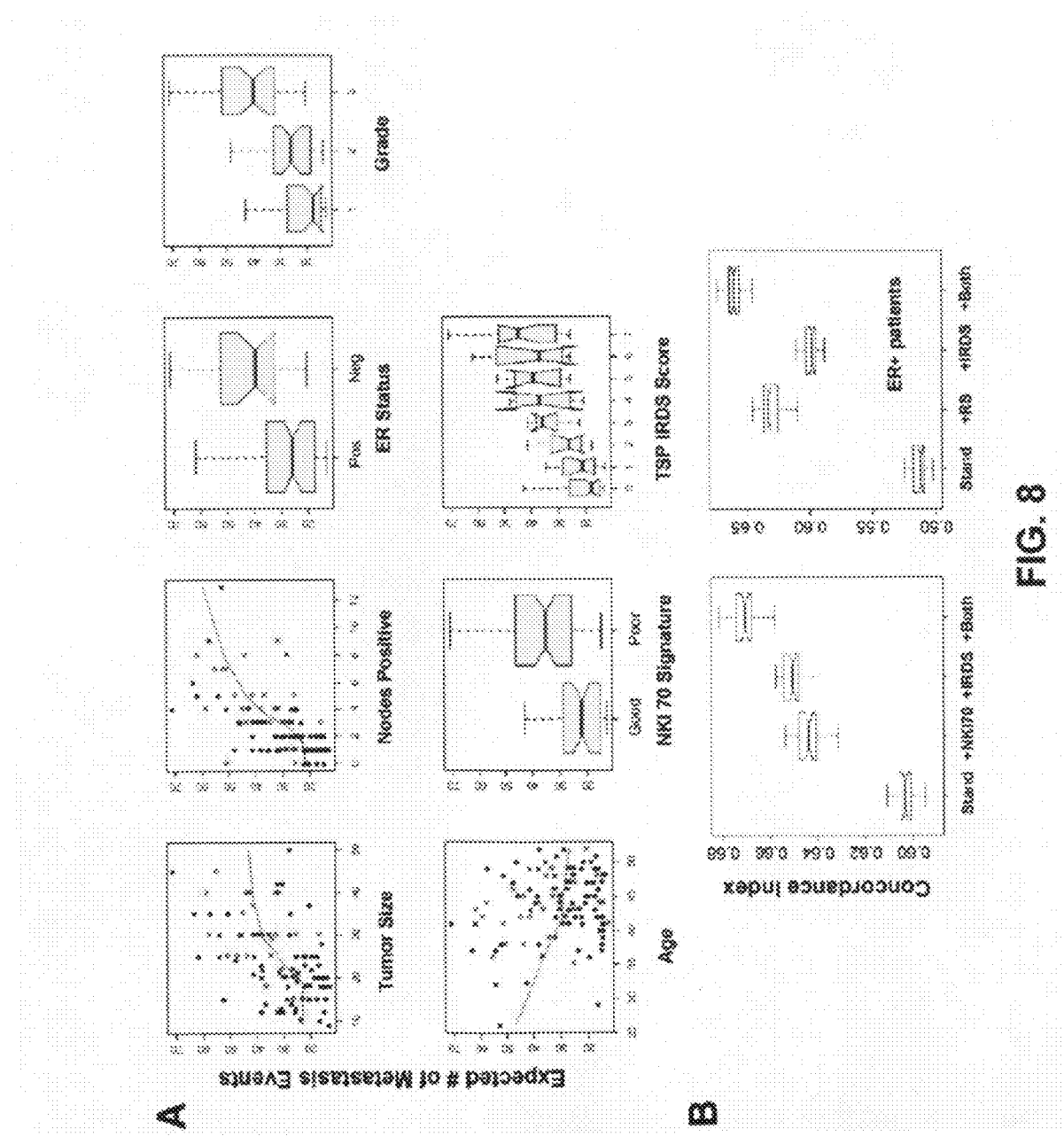
FIG. 8A demonstrates the expected number of metastatic events for each of the indicated standard and genomic markers.
FIG. 8B demonstrates the prediction accuracy by concordance index for adjuvant treated breast cancer patients using random survival forest analysis for standard prognostic markers alone, with NKI 70 gene signature, with TSP IRDS score, and with both NKI 70 gene signature and TSP IRDS score.
FIG. 8C shows concordance index for ER positive patients treated with adjuvant therapy using standard markers, standard markers with the Oncotype DX recurrence score (RS), standard markers with TSP IRDS score, and standard markers with both RS and IRDS score.

8A shows the expected number of metastatic events obtained from the ensemble estimate plotted for each of the indicated covariates. Non-overlapping notches on box and whisker plots are considered significant. This method was also used to provide a concordance index (the proportion of subject pairs in which a subject with a better outcome also has the better predicted outcome) to compare the predictive accuracy of IRDS status to standard tumor markers. FIG. 8B shows box and whisker plot for the concordance index using standard prognostic markers alone (age, tumor size, number of positive lymph nodes, ER status, and grade), with the NKI70 gene signature, with the TSP IRDS score, and with both the NKI70 gene signature and TSP IRDS score. FIG. 8C shows the concordance index for ER positive patients treated with adjuvant chemotherapy using standard markers, standard markers with the Oncotype DX recurrence score (RS), standard markers with the IRDS score, and standard markers with both RS and IRDS score. This analysis revealed that standard prognosis factors (age, grade, tumor size, lymph node positive), the NKI70 gene signature or the RS, and the TSP IRDS score all show a correlation with metastasis free survival among patients treated with adjuvant therapy. When the NKI70 gene signature, the RS, or the TSP IRDS score are added to standard prognosis markers, each individually improve the predictive accuracy as measured by the concordance index, with further improvement if the TSP IRDS score is added in combination. When these analyses were repeated on patients who that had not received adjuvant chemotherapy, the TSP IRDS score did not add to predictive accuracy (data not shown). Thus, TSP IRDS score is a therapy predictive marker that can add to accuracy of both standard prognosis markers and genomic based classifiers.

Example 11

Figure 9:
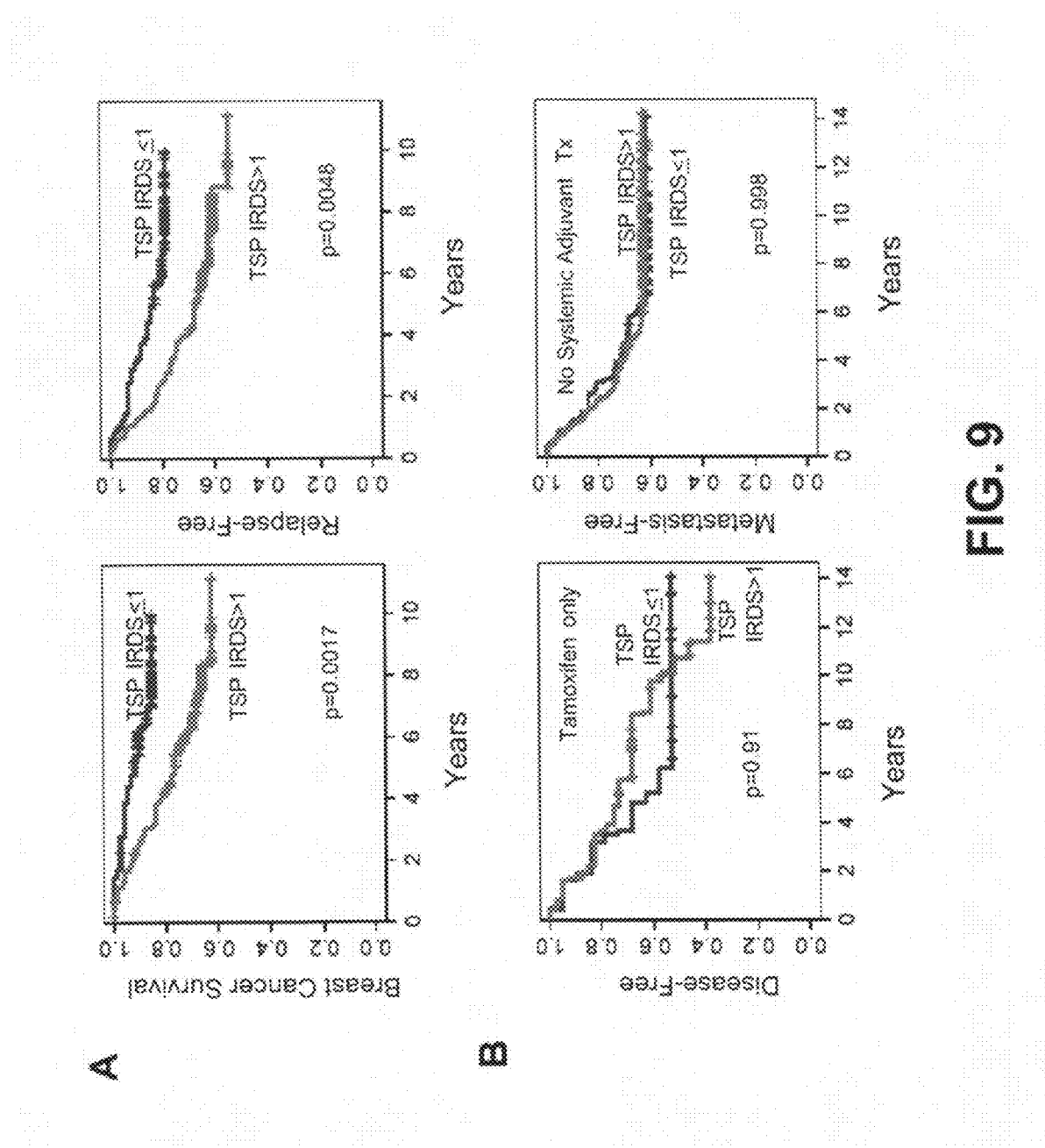
FIG. 9A shows the breast cancer survival curves and relapse-free survival curves using TSP IRDS classifier score for the combined 159 and 99 breast cancer cohort (see Table 2).
FIG. 9B shows the disease free survival curve for 60 breast cancer patients with IRDS scores less than 2 or greater than one that received only endocrine therapy classified by TSP IRDS score.
FIG. 9C shows the metastasis-free survival curve for the 286 breast cancer patients with IRDS scores less than 2 or greater than one that did not receive adjuvant systemic therapy.

Independent Validation of the TSP IRDS Score as a Therapy Predictive Marker for Adjuvant Chemotherapy and Radiation Therapy in Breast Cancer To validate the TSP classifier, the TSP IRDS score was evaluated as a potential therapeutic predictive marker for breast cancer by evaluating breast cancer survival and relapse-free survival as a function of IRDS score. Breast cancer survival was measured using a combined cohort consisting of 159 breast cancer patients (Stockholm 159, see Table 2) and 99 breast cancer patients (Radcliffe 99, see Table 2), 83% of who received adjuvant systemic therapy and 61% radiation therapy. These combined cohorts were stratified by TSP IRDS score less than two or greater than one and the breast cancer survival and relapse-free survival are shown in FIG. 9A. The use of IRDS score as a therapy predictive marker for a non-DNA damaging agent, such as endocrine therapy was tested. A cohort of 60 breast cancer patients (MGH 60, see Table 2) that received only adjuvant endocrine therapy (non-DNA damaging), tamoxifen, were stratified by TSP IRDS score of less than two or greater than one. FIG. 9B shows disease free survival for the breast cancer patients treated with tamoxifen. To test the used of TSP IRDS score in patients not treated with adjuvant therapy, a cohort of 286 breast cancer patients (Erasmus 286, see Table 2) who did not receive adjuvant systemic therapy was given a TSP IRDS score. FIG. 9C shows survival analysis between patients with TSP IRDS scores of two or higher to those patients with scores of 1 or lower. In the cases in which there were genes not expressed on the particular microarray platform (Radcliffe 99, see Table 2), the corresponding gene pair was omitted.

These results indicate that the TSP IRDS score classifier is a therapy predictive marker for adjuvant therapy that involves DNA damaging agents but not endocrine therapy. It is also likely to be a therapeutic predictive marker for adjuvant chemotherapies that act through the interferon pathway and for adjuvant radiation therapy.

Example 12

Figure 11:
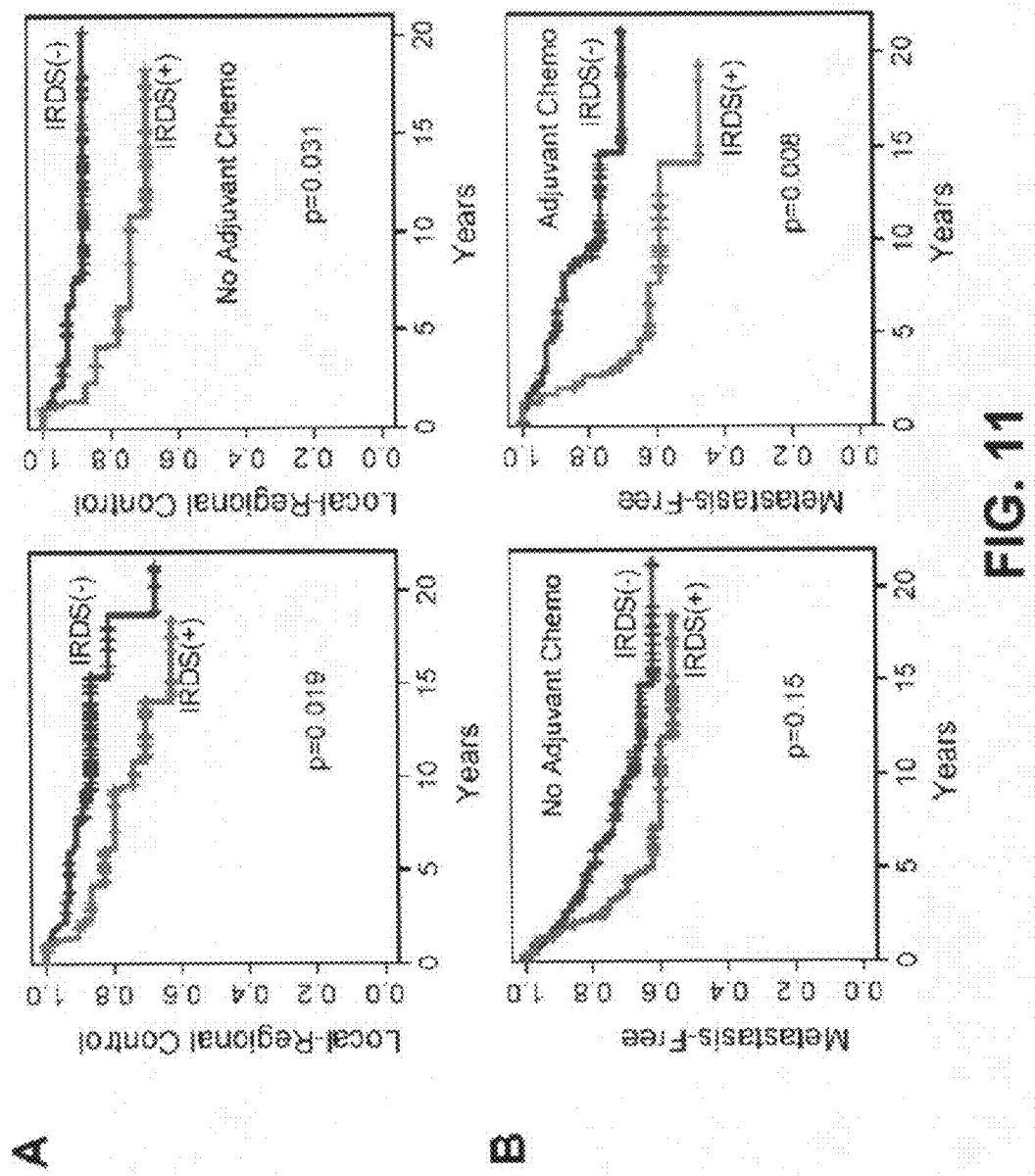
FIG. 11A shows local-regional control survival curves for the IRDS(+) and IRDS(−) subgroups of the 161 patients that received breast conservation and adjuvant radiation treatment.
FIG. 11B shows the metastasis-free survival curves for the IRDS(+) and IRDS(−) subgroups of the 185 breast cancer patients that received no chemotherapy and the 110 breast cancer patients that received adjuvant chemotherapy.

IRDS Status Predicts Benefit of Adjuvant Therapy for Patients with Breast Cancer The use of top scoring pairs (TSP) classifier to determine IRDS status trained by majority vote rather than the use of a clinically determined cut-off and its correlation to outcome was examined for the 295 breast cancer patients in the NKI295 cohort (see Table 2) as described in Example 7. FIG. 11A shows the local-regional survival curves for 161 breast cancer patients that underwent breast conservation either with or without adjuvant chemotherapy. (FIG. 11B shows the metastasis-free survival curves for the IRDS(+) and IRDS(−) 185 breast cancer patients who did not receive adjuvant chemotherapy and the IRDS(+) and IRDS(−) 110 patients who received adjuvant chemotherapy. A greater fraction of IRDS (−) patients receiving adjuvant chemotherapy were metastasis free over time than were IRDS(+) patients. Thus, even without using a clinically determined cut-off, the TSP IRDS classifier is a therapeutic predictive marker for breast cancer patients who receive adjuvant therapy.

Example 13

Figure 12:
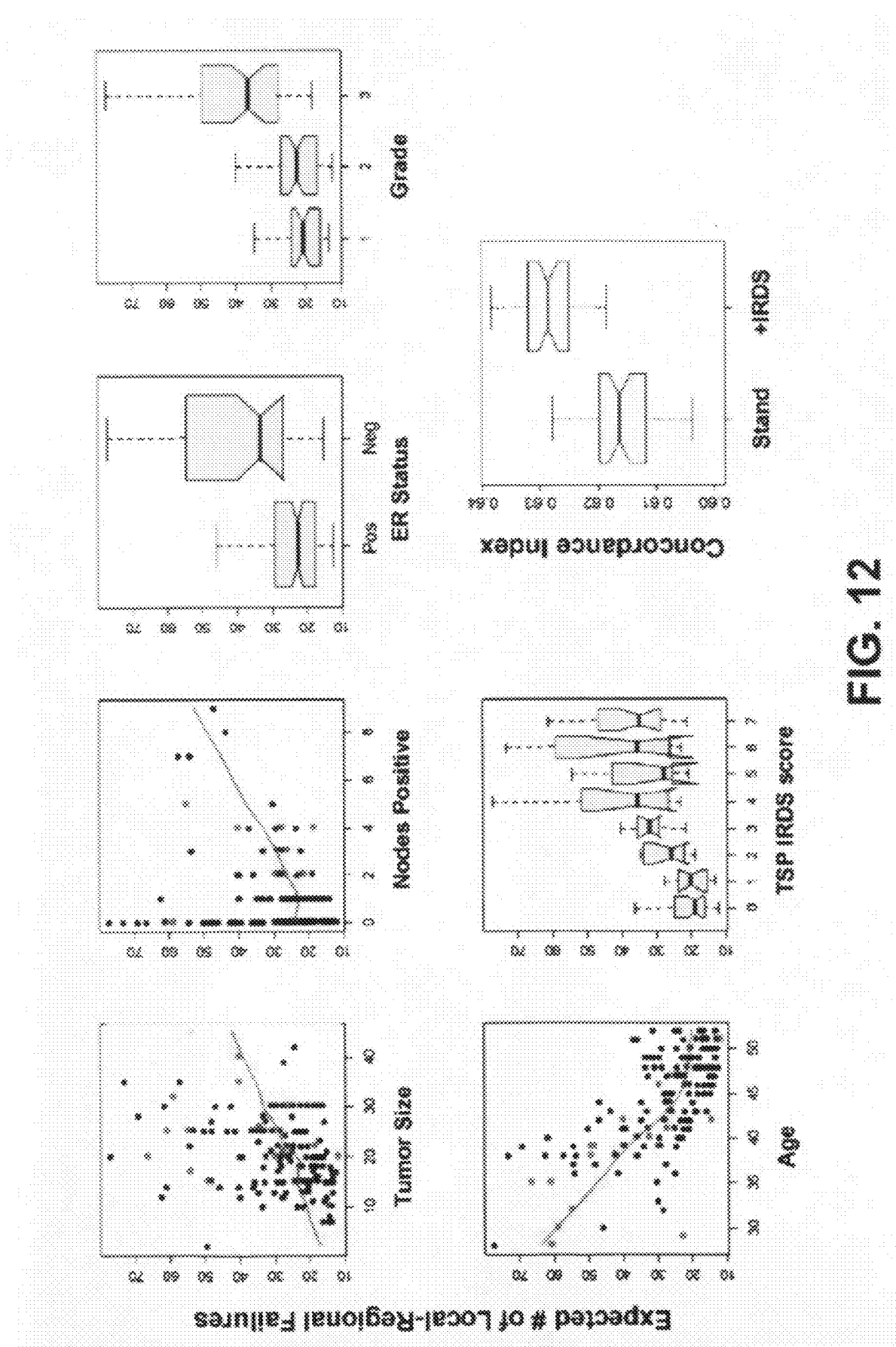
FIG. 12 shows the expected number of local-regional failures by random survival forest analysis for genomic and standard prognostic markers for patients that underwent breast conservation and adjuvant radiation.

IRDS Adds to Standard Prognosis Markers Prediction Accuracy for Local-Regional Failure Among Patients Treated with Breast Conservation Therapy To assess whether the TSP IRDS score adds to the predictive accuracy of standard prognostic markers, the 161 breast cancer patients from the NKI295 cohort who received breast conservation treatment and adjuvant radiation were used in random survival analysis for clinical and pathological markers, and IRDS status as described in Example 10. The expected number of patients with local-regional failure obtained from the ensemble estimate is plotted for each of the indicated covariates in FIG. 12A. Non-overlapping notches on box and whisker plots are considered significant. A box and whisker plot for the concordance index to measure prediction accuracy is shown in FIG. 12B using standard prognostic markers alone (tumor size, number of positive lymph nodes, ER status, and age) or standard markers with TSP IRDS score as described in Example 10.

TSP IRDS scores can enhance accuracy of predicting the expected number of local-regional failures over using just standard prognosis markers.

Example 14

IRDS(+) Tumors Have Aggressive Characteristics 295 breast cancer patients from the 295NKI cohort were analyzed for tumor characteristics as seen in Table 3. The number of patients out of each group (indicated by the columns) is listed for each of the characteristics indicated in the rows. The IRDS(+) tumors had more aggressive characteristics, i.e. ER negative status, grade 2 or 3 status, and NKI70 poor prognosis signature. For categorical data, p-values were calculated by a Chi-square test, and for ordinal data p-values were calculated by either a Student's t-test or by a Wilcox rank sum test for skewed data.

TABLE 3

Breast cancer patient characteristics stratified by IRDS status.

|  | IRDS(−) | IRDS(+) | p-value |
| --- | --- | --- | --- |
| ER negative | 28 | 41 | p = 0.003 |
| Age | 44.2 | 43.7 | p = 0.83 |
| Size | 2.20 | 2.33 | p = 0.54 |
| LN positive | 78 | 66 | p = 0.41 |
| Grade 2, 3 | 110 | 110 | p < 0.001 |
| Hormones | 20 | 20 | p = 0.43 |
| Chemo | 61 | 49 | p = 0.78 |
| NKI70 | 82 | 98 | p < 0.001 |
| Total | 168 | 127 |  |

Example 15

IRDS(−) Breast Cancer Patients Benefit from Adjuvant Chemotherapy for Reducing Distant Metastasis To determine if IRDS status could predict response to adjuvant therapy and risk of metastasis, the NKI295 breast cancer cohort was analyzed. Cox proportional hazards model for distant metastasis controlled for multiple poor prognosis clinical markers was performed on the cohort of breast cancer patients classified as both IRDS(+) (Table 4) and IRDS(−) (Table 5). The proportional hazard assumption of a Cox regression was tested in both cases to ensure that the time-dependent coefficient beta(t) has slope=0 (global p>0.05 in both cases). IRDS(−) patients received significant benefit from adjuvant therapy, whereas IRDS(+) patient received no benefit from chemotherapy. IRDS(−) breast cancer patients receiving adjuvant therapy had reduced risk of distant metastasis.

TABLE 4

IRDS(−) patients only: Cox model for distant metastasis.

|  | HR | lower | upper | p-value |
| --- | --- | --- | --- | --- |
| Chemo | 0.429 | 0.211 | 0.873 | 0.020 |
| ER negative | 1.737 | 0.852 | 3.540 | 0.130 |
| Grade 2, 3 | 3.067 | 1.255 | 7.494 | 0.014 |
| Age | 0.951 | 0.899 | 1.007 | 0.083 |
| Nodes | 1.183 | 1.060 | 1.320 | 0.003 |
| Size | 1.037 | 1.006 | 1.069 | 0.018 |
| Hormones | 0.282 | 0.037 | 2.127 | 0.220 |

TABLE 5

IRDS(+) patients only: Cox model for distant metastasis.

|  | HR | lower | upper | p-value |
| --- | --- | --- | --- | --- |
| Chemo | 0.814 | 0.380 | 1.740 | 0.600 |
| ER negative | 1.176 | 0.606 | 2.280 | 0.630 |
| Grade 2, 3 | 1.657 | 0.582 | 4.720 | 0.340 |
| Age | 0.983 | 0.930 | 1.040 | 0.540 |
| Nodes | 1.031 | 0.889 | 1.200 | 0.690 |
| Size | 1.034 | 1.001 | 1.070 | 0.043 |
| Hormones | 0.806 | 0.336 | 1.930 | 0.630 |

While the compositions and methods of this invention have been described in terms of exemplary embodiments, it will be apparent to those skilled in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention. In addition, all patents and publications listed or described herein are incorporated in their entirety by reference.

As used in this specification and the appended claims, the singular forms "a," "an," and "the" include plural referents unless the content clearly dictates otherwise. Thus, for example, reference to a composition containing "a polynucleotide" includes a mixture of two or more polynucleotides. It should also be noted that the term "or" is generally employed in its sense including "and/or" unless the content clearly dictates otherwise. All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical value recited herein includes all values from the lower value to the upper value, i.e., all possible combinations of numerical values between the lowest value and the highest value enumerated are to be considered to be expressly stated in this application.

We claim:

1. A method of determining the IRDS status of a tumor from a patient comprising detecting expression of seven or more IRDS-markers of Table 1 by the tumor, wherein the seven or more IRDS-markers includes at least IFIT3, STAT1, IFIT1, OAS1, IF144, MX1, and G1P2, wherein increased expression of mRNA of upregulated IRDS markers of Table 1 and/or decreased expression of mRNA of downregulated IRDS markers of Table 1 relative to a reference indicates that the tumor is IRDS positive, and the absence of increased expression of mRNA of the upregulated IRDS markers and the absence of decreased expression of mRNA of the downregulated IRDS markers indicates that the tumor is IRDS negative.

2. The method of claim 1, wherein the tumor is selected from the group consisting of lung cancer, prostate cancer, testicular cancer, brain cancer, skin cancer, colon cancer, rectal cancer, gastric cancer, esophageal cancer, tracheal cancer, head and neck cancer, pancreatic cancer, liver cancer, breast cancer, ovarian cancer, lymphoid cancer, kidney cancer, cervical cancer, bone cancer, vulvar cancer and melanoma.

3. The method of claim 1 further comprising determining the status of a prognosis factor.

4. The method of claim 3 wherein the prognosis factor comprises age, grade of tumor, tumor size, lymph node status or distant metastasis.

5. The method of claim 3 wherein the prognosis factor comprises expression of at least one marker from the NKI70 gene signature.

6. The method of claim 3 wherein the prognosis factor comprises expression of at least one lung metastatic marker.

7. The method of claim 1, wherein the IRDS status is assigned by calculating an IRDS score using a top scoring pair method, each top scoring pair including an IRDS marker from Table 1.

8. The method of claim 7, wherein at least one top scoring pair includes at least one IRDS marker selected from the group consisting of IFIT3, STAT1, IFIT1, OAS1, IF144, MX1, and G1P2, and wherein the IRDS status is predictive of tumor response to at least one chemotherapeutic agent or radiation.

9. The method of claim 1, further comprising using the IRDS status to predict tumor response to a chemotherapeutic agent selected from DNA damaging agents and modulators of an interferon pathway, or to radiation administered to the patient.

10. The method of claim 9, wherein an IRDS positive status is indicative of tumor resistance to the chemotherapeutic agent or radiation.

11. The method of claim 9 wherein an IRDS negative status is indicative of tumor sensitivity to the chemotherapeutic agent or radiation.

12. The method of claim 9, wherein the chemotherapeutic agent is a DNA damaging agent.

13. The method of claim 9, wherein the chemotherapeutic agent is a direct or indirect modulator of an interferon pathway.

14. The method of claim 9, further comprising determining a cancer patient treatment protocol based on the predicted tumor response.

15. The method of claim 1, wherein the IRDS status is used to determine a prognosis for the cancer in the patient.

16. The method of claim 15, wherein the prognosis comprises relative survival rate.

17. The method of claim 15, wherein the prognosis comprises relative risk of metastasis.

18. The method of claim 15, wherein the prognosis comprises relative risk of local-regional failure.

19. The method of claim 2, wherein the tumor is a breast cancer tumor.

20. The method of claim 2, wherein the tumor is a brain cancer tumor.

21. The method of claim 1, wherein the mRNA levels are detected directly, or indirectly, following reverse transcription of mRNA.

22. The method of claim 21, wherein levels are detected using DNA microarray analysis or a real time reverse transcription PCR.

23. The method of claim 9, wherein the IRDS status is used to predict tumor response to radiation.

* * * * *